(12) United States Patent
Schlyer et al.

(10) Patent No.: US 7,091,489 B2
(45) Date of Patent: Aug. 15, 2006

(54) POSITRON EMISSION TOMOGRAPHY WRIST DETECTOR

(75) Inventors: David J. Schlyer, Bellport, NY (US); Paul O'Connor, Bellport, NY (US); Craig Woody, Setauket, NY (US); Sachin Shrirang Junnarkar, Sound Beach, NY (US); Veljko Radeka, Bellport, NY (US); Paul Vaska, Sound Beach, NY (US); Jean-Francois Pratte, Stony Brook, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 465 days.

(21) Appl. No.: 10/688,577

(22) Filed: Oct. 16, 2003

(65) Prior Publication Data
US 2005/0167599 A1    Aug. 4, 2005

(51) Int. Cl.
*G01T 1/164* (2006.01)
(52) U.S. Cl. ................................. 250/363.03
(58) Field of Classification Search ........... 250/363.03, 250/363.04, 369
See application file for complete search history.

(56) References Cited

U.S. PATENT DOCUMENTS

| 4,864,140 A | 9/1989 | Rogers et al. |
| 5,793,254 A | 8/1998 | O'Connor |
| 2004/0195512 A1* | 10/2004 | Crosetto ................. 250/363.04 |

OTHER PUBLICATIONS

J.-F. Pratte, et al. "Design of a Fast-Shaping Amplifier for PET/CT APD Detectors with Depth-of-Interaction", *IEEE Transactions on Nuclear Science*, vol. 49, No. 5, pp. 2448-2454, Oct. 5, 2002.

Paul O'Connor, et al., "Prospects for Charge Sensitive Amplifiers in Scaled CMOS", *Nuclear Instruments and Methods in Physics Research*, Section A, vol. 480, pp. 713-725, Mar. 27, 2002.

G. De Geronimo, et al., "Front-End Electronics for Imaging Detectors", *Nuclear Instruments and Methods in Physics Research*, Section A, vol. 471, pp. 192-199 (2001).

P. Vaska, et al., "Effects of Inter-Crystal Cross-Talk on Multi-Element LSO/APD PET Detectors", pp. 1-3, Apr. 19, 2002.

A. Kriplani, et al., "Comparison of Experimentally Measured Light Output with Monte Carlo Simulations from LSO Crystals", pp. 1-2 (2001).

(Continued)

*Primary Examiner*—David Porta
*Assistant Examiner*—Marcus Taningco
(74) *Attorney, Agent, or Firm*—Margaret C. Bogosian

(57) ABSTRACT

A method of serially transferring annihilation information in a compact positron emission tomography (PET) scanner includes generating a time signal representing a time-of-occurrence of an annihilation event, generating an address signal representing a channel detecting the annihilation event, and generating a channel signal including the time and address signals. The method also includes generating a composite signal including the channel signal and another similarly generated channel signal concerning another annihilation event. An apparatus that serially transfers annihilation information includes a time signal generator, address signal generator, channel signal generator, and composite signal generator. The time signal is asynchronous and the address signal is synchronous to a clock signal. A PET scanner includes a scintillation array, detection array, front-end array, and a serial encoder. The serial encoders include the time signal generator, address signal generator, channel signal generator, and composite signal generator.

40 Claims, 39 Drawing Sheets

OTHER PUBLICATIONS

C. Woody, et al., "RatCAP: A Small, Head-Mounted PET Tomograph for Imaging the Brain of an Awake RAT", *Elsevier Science*, pp. 1-4, May 2003.

P. Vaska, et al., "RatCAP: Miniaturized Head-Mounted PET for Conscious Rodent Brain Imaging", pp. 1-2 manuscript received May 16, 2003.

S. Shokouhi, et al., "System Performance Simulations of the RatCAP Awake Rat Brain Scanner", pp. 1-2, Oct. 2003.

B.J. Pichler, et al., "A 32-Channel LSO Matrix Coupled to a Monolithic 4×8 APD Array for High Resolution PET", Abstract, *Proceedings of 2000 IEEE Med. Imag. Conf.* (2000).

G. De Geronimo, et al., "A CMOS Fully Compensated Continuous Reset System", *IEEE Transactions on Nuclear Science*, vol. 47, No. 4, pp. 1458-1462, Aug. 2000.

P. Vaska, et al., "Imaging the Unanesthetized Rat Brain with PET: A Feasibility Study", *IEEE*, pp. 1569-1571 (2002).

S. Shokouhi, et al., "A Non-invasive LSO-APD Blood Radioactivity Monitor for PET Imaging Studies", pp. 1-5, Nov. 10, 2002.

S.R. Cherry, et al., "MicroPET: A High Resolution PET Scanner for Imaging Small Animals", *IEEE Transactions on Nuclear Science*, vol. 44, No. 3, pp. 1161-1166, Jun. 1997.

S. Shokouhi, et al., "A Non-invasive LSO-APD Blood Radioactivity Monitor for PET Imaging Studies", pp. 1-2 (2002).

S. Shokouhi, et al., "A Non-invasive LSO-APD Blood Radioactivity Monitor for PET Imaging Studies", pp. 1-2 (2003).

A. Villanueva Jr., et al., "Spatial Resolution of a Noninvasive Measurement of the Arterial and Venous Input Function Using a Wrist Monitor", pp. 1-2, Oct. 2003.

J.F. Pratte, et al., "Front-end Electronics for the RatCAP Mobile Animal Pet Scanner", pp. 1-2, Oct. 2003.

P. Vaska, et al., "Imaging the Unanesthetized Rat Brain with PET: A Feasibility Study", pp. 1-2, Apr. 20, 2001.

A. Chatziioannou, et al., "Performance Evaluation of microPET: A High-Resolution Lutetium Oxyorthosilicate PET Scanner for Animal Imaging", *The Journal of Nuclear Medicine*, vol. 20, No. 7, pp. 1164-1175, Jul. 1999.

P. van Zant, "Chapter 5: Overview of Wafer Fabrication", *Microchip Fabrication*, 3$^{rd}$ edition, pp. 99-118 (1997).

P. O'Connor, et al., "Low Noise Charge Amplifiers in Submicron CMOS", 5$^{th}$ International Workshop on Front End Electronics, pp. 1-21, Jul. 2, 2003.

P. Vaska, et al., "A Practical and Competitive Alternative of Mega-Crystal PET: A Miniature Anger Detector with LSO and APDs", Jun. 2001.

C. Woody, "New Detectors for PET Imaging of Small, Awake Animals", Instrumentation Seminar, pp. 1-50, Mar. 12, 2003.

"Scanning Lab Rats as they Scurry", Popular Mechanics, p. 22, Aug. 2003.

"Électronique Du Scanner Pet", Oct. 2002.

* cited by examiner

Individual Serial Links

Common Serial Bus with Busy

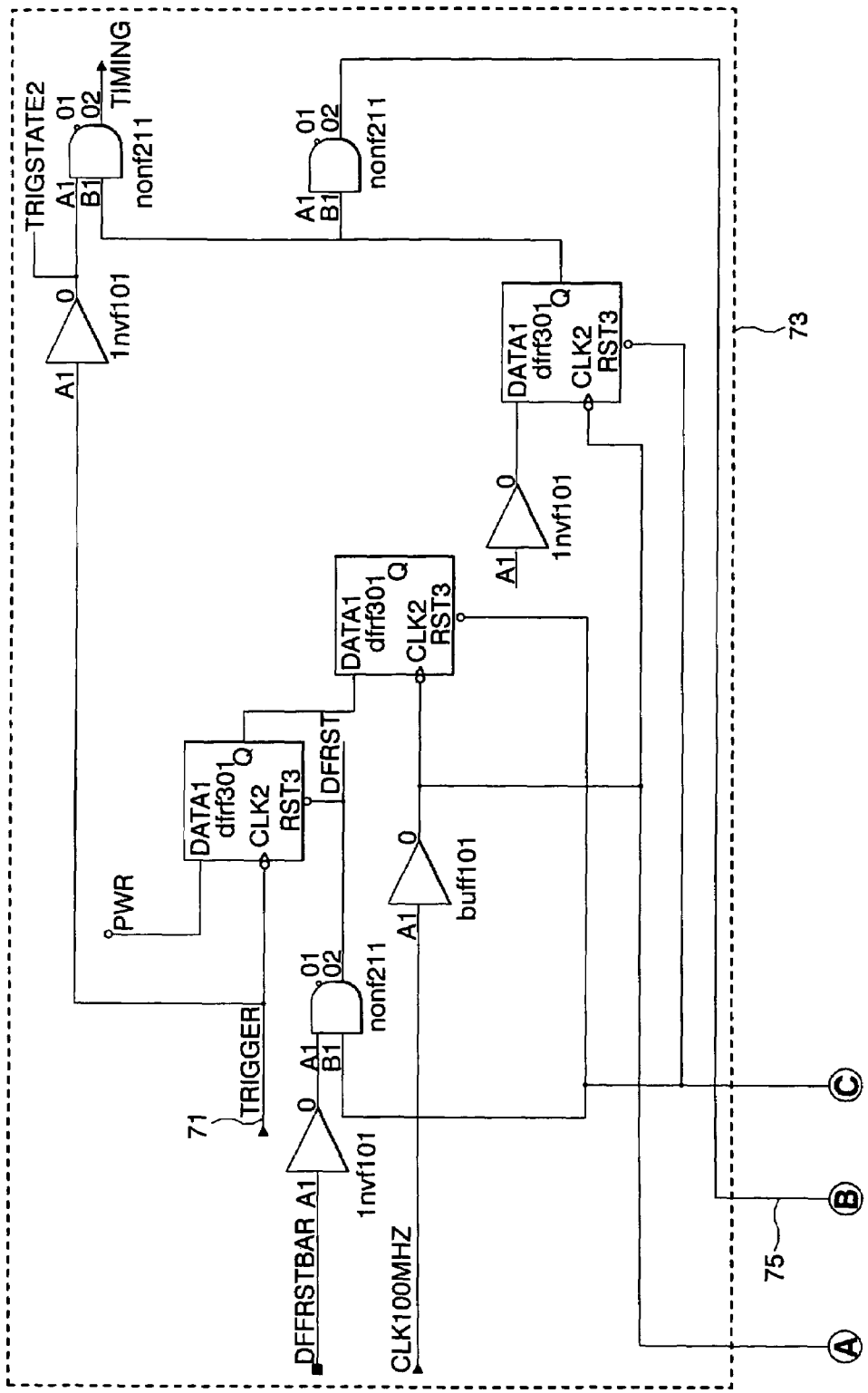
Figure 12a(1)

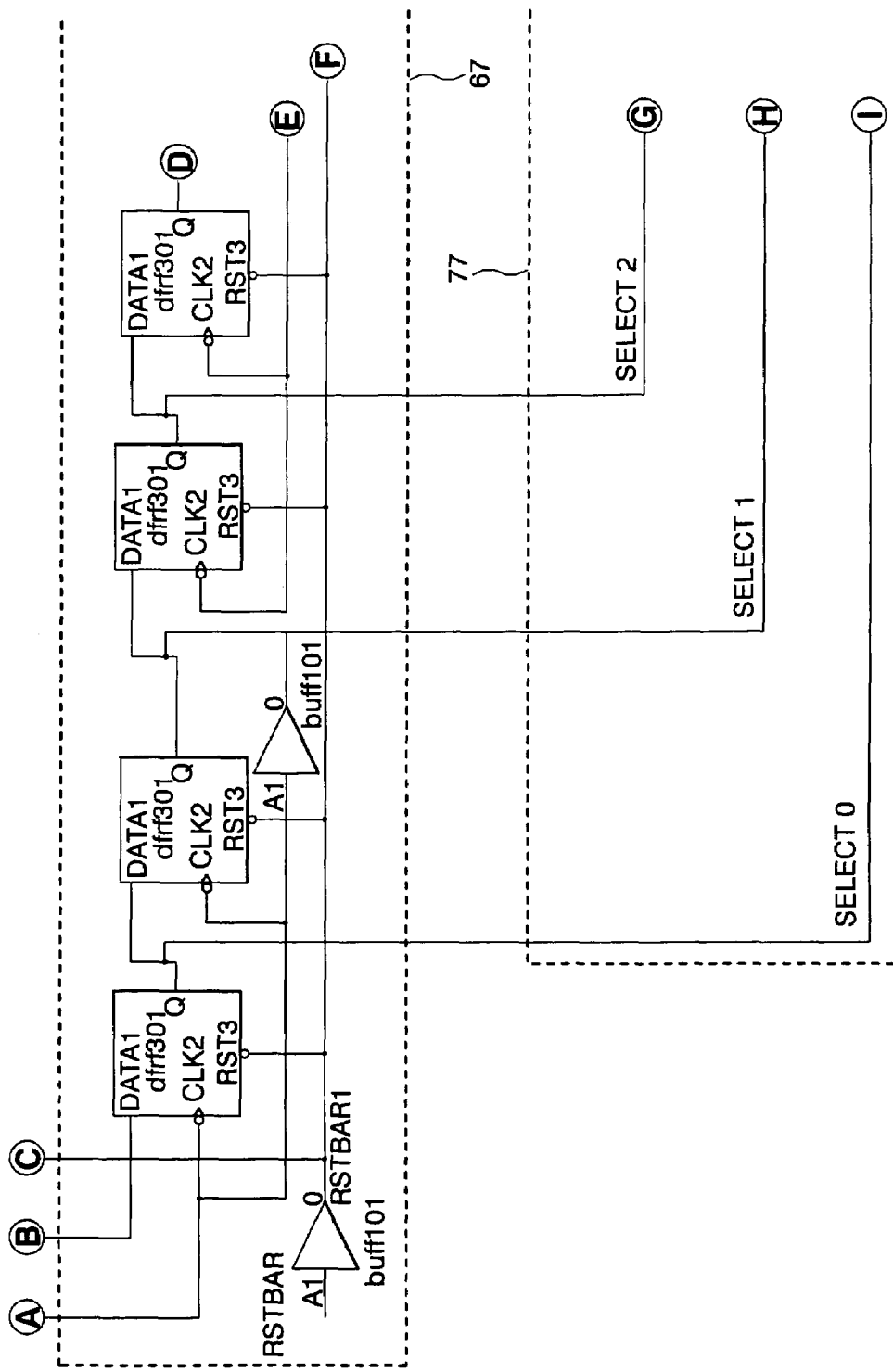
Figure 12a(2)
TRIGGER = Asynchronous Trigger
A [4.0] = 5 Bit Crystal ID from the 32 to 5 Priority Encoder
SERADD - serialized 5 bit Crystal ID at 100MHz

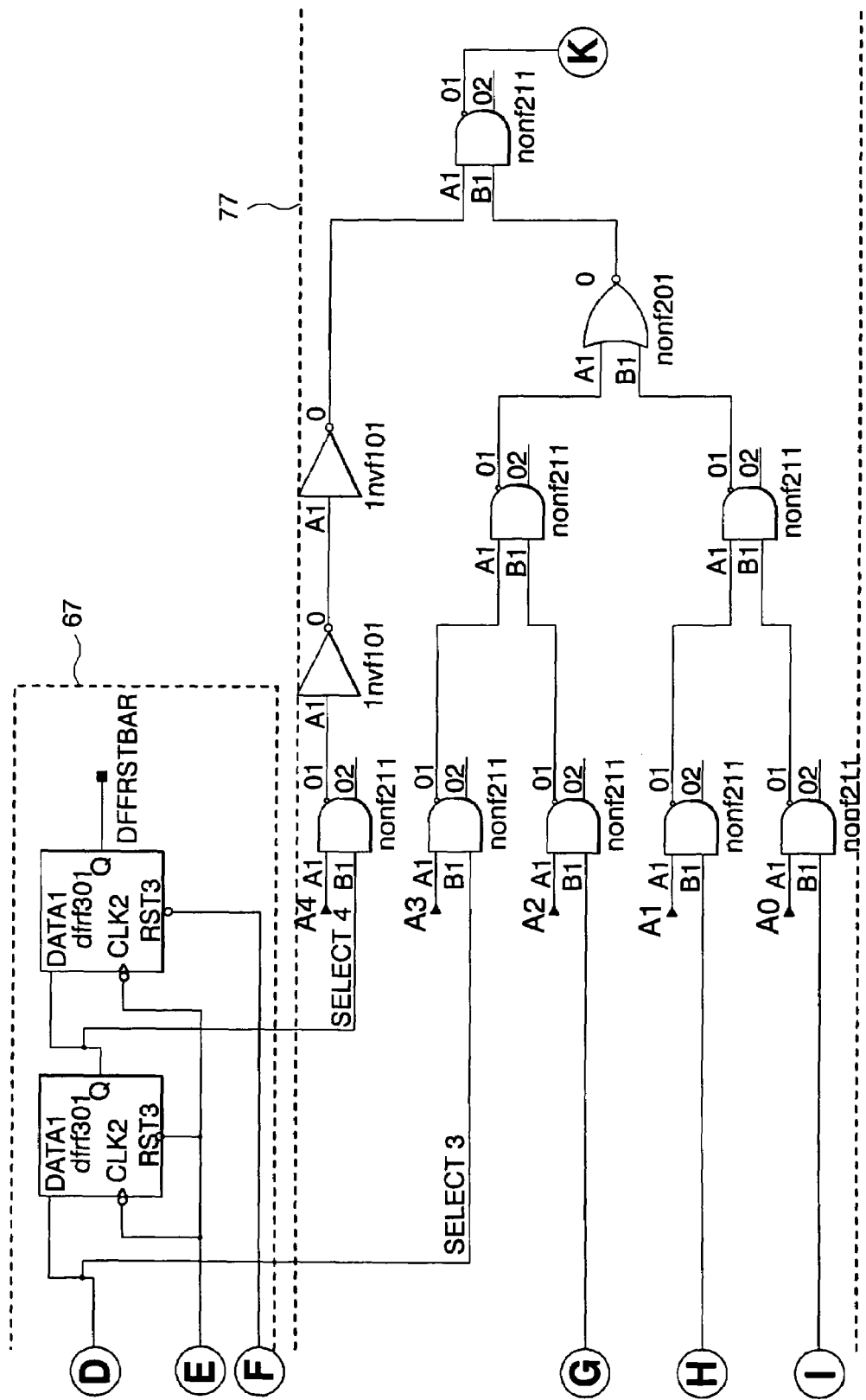
Figure 12a(3)

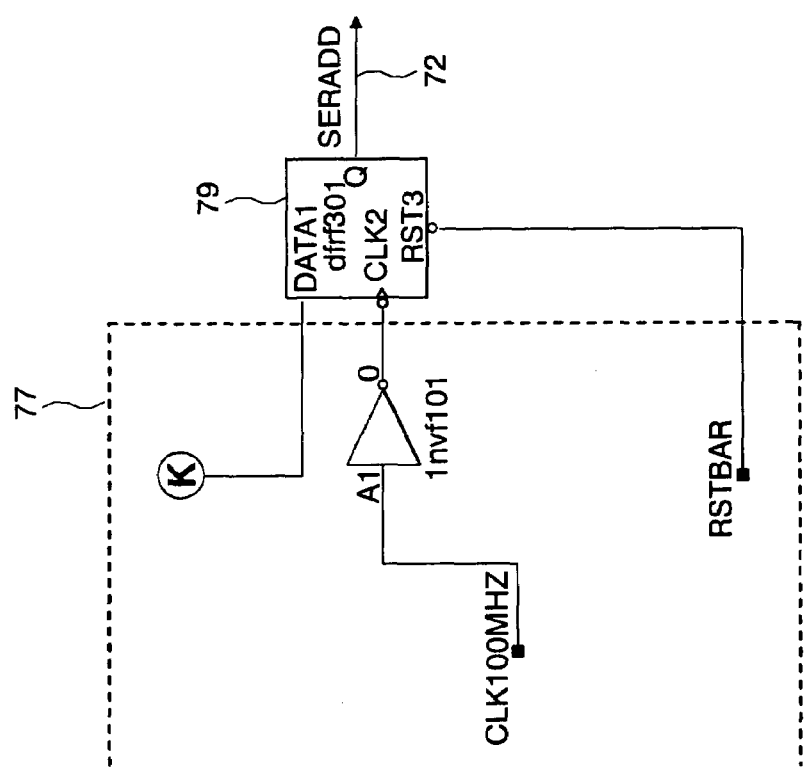
Figure 12a(4)

POSITRON EMISSION TOMOGRAPHY WRIST DETECTOR

This invention was made with Government support under contract number DE-AC02-98CH10886, awarded by the U.S. Department of Energy. The Government has certain rights in the invention.

BACKGROUND OF THE INVENTION

1. Field of the Invention

The present invention relates to positron emission tomography (PET) scanners, and more particularly to low-power, low-noise compact PET scanners for use in obtaining an input function from a portion of the human body, such as the wrist.

2. Description of the Prior Art

Positron emission tomography (PET) scanning is a diagnostic tool for non-invasively imaging living organisms. It remains essential to the investigation of chemical and functional processes in biochemistry, biology, physiology, anatomy, molecular biology, and pharmacology. While techniques, such as x-rays, computed tomography (CT), and magnetic resonance imaging (MRI) provide anatomical images, PET scanning provides insight into biochemical changes that generally occur long before a corresponding structural change is detectable by more traditional techniques.

Positrons are positively charged electrons emitted by the nucleus of an unstable radioisotope. The radioisotope is unstable because it is positively charged and has too many protons. Release of the positron stabilizes the radioisotope by converting a proton into a neutron. For radioisotopes used in PET, the element formed from positron decay is stable. All radioisotopes used in PET decay by positron emission. The positron travels a small distance, which depends on its energy, before combining with an electron during a so-called "annihilation event". The annihilation event ultimately converts the mass of the positron and electron into two gamma rays that are emitted at 180° to each other along a so-called "line of coincidence". These gamma rays are readily detectable outside the human body.

A small amount of the unstable radioisotope is typically administered to the patient by injection or inhalation, following which it circulates through the body. Scintillation crystals in a tomograph detect the gamma rays emitted by the radioisotope and convert them to light photons. The light photons are then converted to electrical impulses that are processed by the tomograph to determine the location of the annihilation event as being along the line of coincidence.

Kinetic imaging or modeling measures the uptake of a tracer isotope over a period of time. The distribution of tracer isotopes may be used to represent regional blood flow and glucose metabolism. These studies often require catheterization to obtain discrete blood samples, which are analyzed for radioactivity and radioisotope metabolism. Unfortunately, the invasive withdrawal of blood is a significant discomfort to the patient, as well as a significant health risk for both the patient and hospital personnel through exposure to blood borne diseases and radioactive contamination. Therefore, direct arterial blood sampling is considered a health risk for both patients and health workers.

A wide range of quantitative PET studies using tracer kinetic modeling require accurately measured radiotracer concentrations in arterial blood as a function of time after injection, which is commonly referred to as an "arterial input function". To circumvent the health risks associated with direct arterial blood sampling, several approaches have been examined in an effort to non-invasively obtain an accurate arterial input function. While some approaches have focused primarily on the use of tomography, others have examined additional detector systems that generate a quantitative image-derived input function.

Using the tomograph, studies have examined the possibility of obtaining an input function using large blood vessel imaging. However, this approach is limited in several respects. First, tomography exhibits a partial volume effect defined by spatial resolution. However, an artery large enough to provide reliable data may not be in the field of view. Second, time resolution may be determined by frame acquisition rates specified for a particular study. Although list mode acquisition capabilities reduce restrictions associated with slower acquisition rates, many scanners do not have this capability. Third, subject placement within the tomograph may affect the accuracy of the input function and obtaining reproducible positioning of the body is difficult.

An alternative approach involves placing a radioactivity detector directly over a blood vessel or lung. The primary disadvantage of this approach is the substantial background associated with the surrounding tissue. This background must be subtracted to obtain the true input function. Since this approach is not based on coincidence counts, the signal may include a substantial amount of noise.

Another alternative is to use a standardized input function, which is averaged across many subjects, or a modeled input function. In the latter method, the input function is calculated from various physiological parameters. However, since the input function is very dependent on individual physiological states and procedural variables, such as differences in injection rates, these methods may lead to inaccurate results. Therefore, each of the techniques discussed above yield potential errors and there is a distinct need to determine accurate input functions by measuring the blood activity with little background from remaining portions of the body.

Compact PET detectors require an efficient method of transmitting signals from the detectors to remote electronics for off-line processing. Conventional detectors communicate via independent data links, each of which is dedicated to a particular channel. However, since the majority of PET detectors include hundreds or even thousands of channels, this technique is too cumbersome for a compact PET detector.

OBJECTS AND SUMMARY OF THE INVENTION

It is an object of the present invention to provide a method and apparatus that reduce the discomfort of a patient, the risk associated with blood borne pathogens, and radioactive dispersion from the collection of blood samples typically required in kinetic modeling Positron Emission Tomography (PET) studies.

It is another object of the present invention to provide a low-noise, low-power method and apparatus that are capable of non-invasively, selectively, and accurately measuring arterial radioactivity.

It is yet another object of the present invention to provide a method and apparatus that maximize detector efficiency and spatial resolution by separating arterial information from venous and surrounding tissue information during PET scanning.

It is a further object of the present invention to provide a method and apparatus that utilize improved timing resolution and selective shielding techniques to effectively reduce random coincidence during PET scanning.

A method of serially transferring annihilation information in a compact positron emission tomography (PET) scanner used to obtain an input function from at least a portion of a human body in accordance with one form of the present invention, which incorporates some of the preferred features, includes the steps of inputting a first time pulse on a first channel, and generating a first time signal representing the time-of-occurrence of the first time pulse and a first annihilation event. The method also includes generating a first address signal including a first address representing the first channel, generating a first channel signal including the first time signal and the first address signal, and outputting the first channel signal serially.

The first time pulse is asynchronous to a clock signal and the first address signal is synchronous to the clock signal. The method may also include the steps of generating a composite signal including the first channel signal and a similarly generated second channel signal concerning a second annihilation event, and outputting the composite signal serially.

An apparatus to serially transfer annihilation information in a compact positron emission tomography (PET) scanner used to obtain an input function from at least a portion of a human body in accordance with one form of the present invention, which incorporates some of the preferred features, includes a first time signal generator, a first address signal generator, and a first channel signal generator. The first time signal generator inputs a first time pulse on a first channel, which includes a position representing a time-of-occurrence of a first annihilation event. The first time signal generator generates a first time signal representing the time-of-occurrence of the first time pulse and the first annihilation event. The first time pulse is asynchronous to a clock signal.

The first address signal generator generates a first address, which represents the first channel, and a first address signal, which includes the first address. The first address signal is synchronous to the clock signal. The first channel signal generator generates a first channel signal including the first time signal and the first address signal, and outputs the first channel signal serially.

A compact positron emission tomography (PET) scanner used to obtain an input function from at least a portion of a human body, which incorporates some of the preferred features, includes a scintillation array, detection array, front-end array, and serial encoder. The scintillation array includes a plurality of crystals and outputs photons in response to receiving gamma radiation from an annihilation event. The detection array includes a plurality of detectors and outputs a detection signal in response to detecting the photon.

The front-end array includes a plurality of front ends and outputs a time pulse in response to receiving the detection signal. The serial encoder includes a time signal generator, address signal generator, and channel signal generator.

These and other objects, features, and advantages of this invention will become apparent from the following detailed description of illustrative embodiments thereof, which is to be read in connection with the accompanying drawings.

BRIEF DESCRIPTION OF THE DRAWINGS

FIG. 12a is a schematic diagram of a preferred embodiment of the serial encoding circuitry shown in FIG. 12 implemented in an Application Specific Integrated Circuit (ASIC).

DETAILED DESCRIPTION OF THE PREFERRED EMBODIMENTS

A quantitative positron emission tomography (PET) imaging experiment generally requires inserting an arterial catheter, taking blood samples, and analyzing these samples for radioactivity concentration. The method and apparatus formed in accordance with the present invention measures the radioactivity present in the blood without the use of a catheter to physically remove the blood from the artery and mathematically corrects the results of this measurement to accurately represent an arterial input function.

Figure 1:
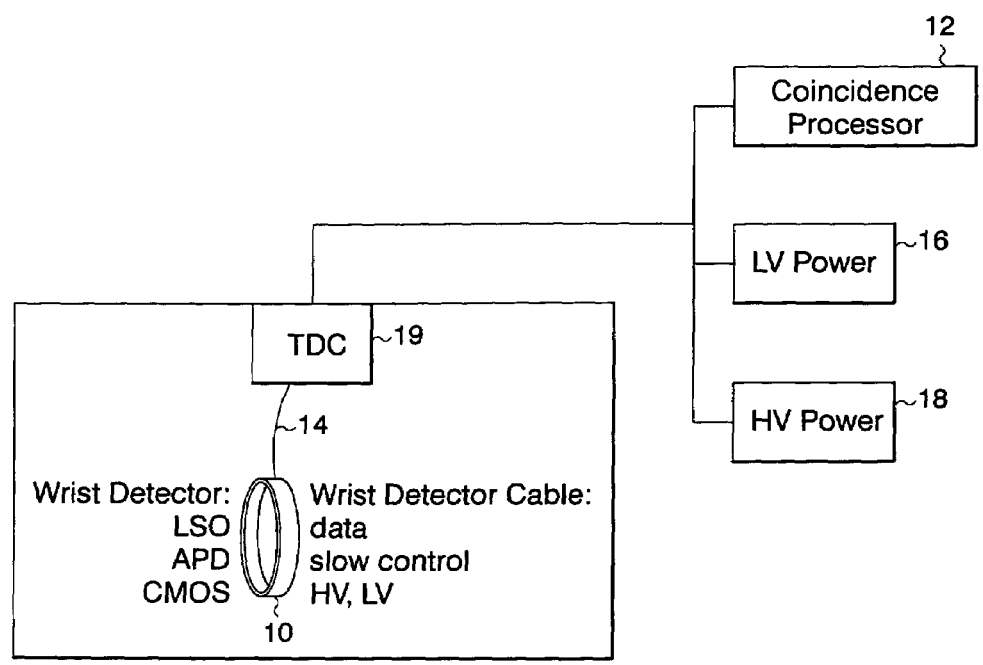
FIG. 1 is a block diagram of a Positron Emission Tomography (PET) system, which includes a wrist detector formed in accordance with the present invention.

The wrist detector system formed in accordance with the present invention provides an accurate arterial input function in the presence of background activity from the body. FIG. 1 is a block diagram showing the wrist detector 10 used in conjunction with a PET scanning system to determine the timing and location of annihilation events.

The system preferably includes a coincidence processor 12 that receives data from the wrist detector 10 through a Time-to-Digital Converter (TDC) 19 and a wrist detector cable 14. The TDC 19 preferably detects a timing edge with corresponding channel and block address information from the wrist detector 10 corresponding to a particular annihilation event. This information is then stored by the coincidence processor 12. Power is preferably provided to the wrist detector 10 through the wrist detector cable 14 by a Low Voltage (LV) power supply 16 and a High Voltage (HV) power supply 18. The TDC 19 translates asynchronous timing pulses representing the time-of-occurrence of an annihilation event into digital information, such as a timestamp, which is used by the coincidence processor 12 to establish coincidence.

Figure 2A:
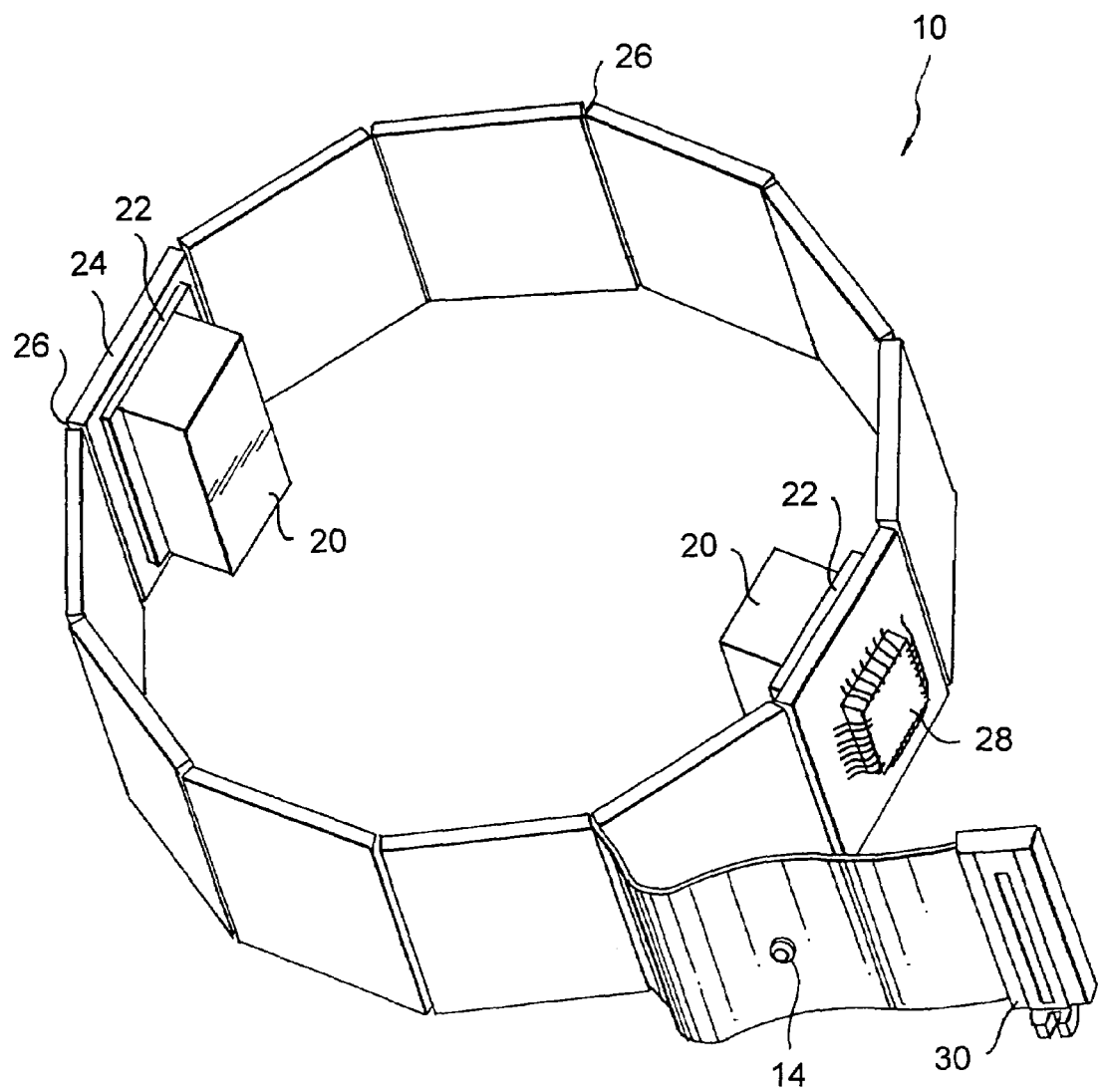
FIG. 2a is a pictorial view of a preferred embodiment of the wrist detector formed in accordance with the present invention.
Figure 3:
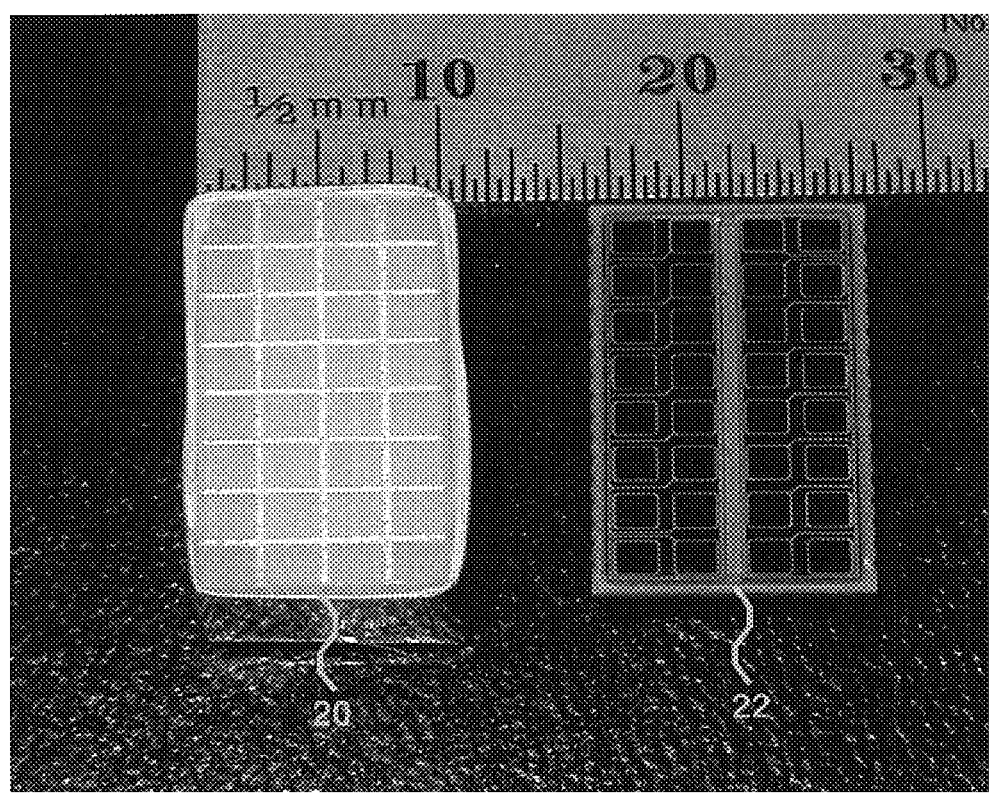
FIG. 3 is a pictorial view of an LSO crystal array and an APD detector array used for measurement of an input function in the wrist detector formed in accordance with the present invention.

FIG. 2a is a pictorial view of a preferred embodiment of the wrist detector 10, which includes two arrays of Lutetium Oxyorthosilicate (LSO) scintillation crystals 20 and two corresponding arrays of avalanche photodiode (APD) detectors 22. An LSO crystal array 20 and an APD detector array 22 are also shown in FIG. 3. A conventional technique has been used with Bismuth Germanate (BGO) crystals and photomultipliers, which exhibits lower spatial resolution. However, such a device exhibits substantial inaccuracies as a result of large partial volume effects. LSO crystals have a detection efficiency similar to that of BGO, but have a faster scintillation decay interval, which is critical for reducing deadtime losses.

In addition, the high stopping power of LSO crystals is ideal when using smaller crystal elements, which improves the spatial resolution of the detector. Spatial resolution is critical for imaging small arteries in the wrist. It is to be noted that although the description of the present invention is directed to a wrist detector, with modifications in size, placement, resolution, and other parameters, the detector may alternatively be used to image additional portions of the human body, such as the head, neck, arm, and leg while remaining within the scope of the present invention.

The spatial resolution of the LSO crystal array 20 approaches theoretical limits due to positron range, which is about 1 mm. The compact size of the APD detector array 22 is also an advantage when used in the limited space of a clinical scanner. As shown in FIG. 3, the one-to-one correspondence between the elements of the LSO crystal array 20 and the APD detector array 22 is advantageous in identifying the point of gamma conversion. Thus, the compact size of each of the APD detectors combined with the potential for mounting multiple APD detectors in an array, provide a unique and compact multi-module detector that is not conventionally achievable with larger photomultiplier block detectors.

Figure 2B:
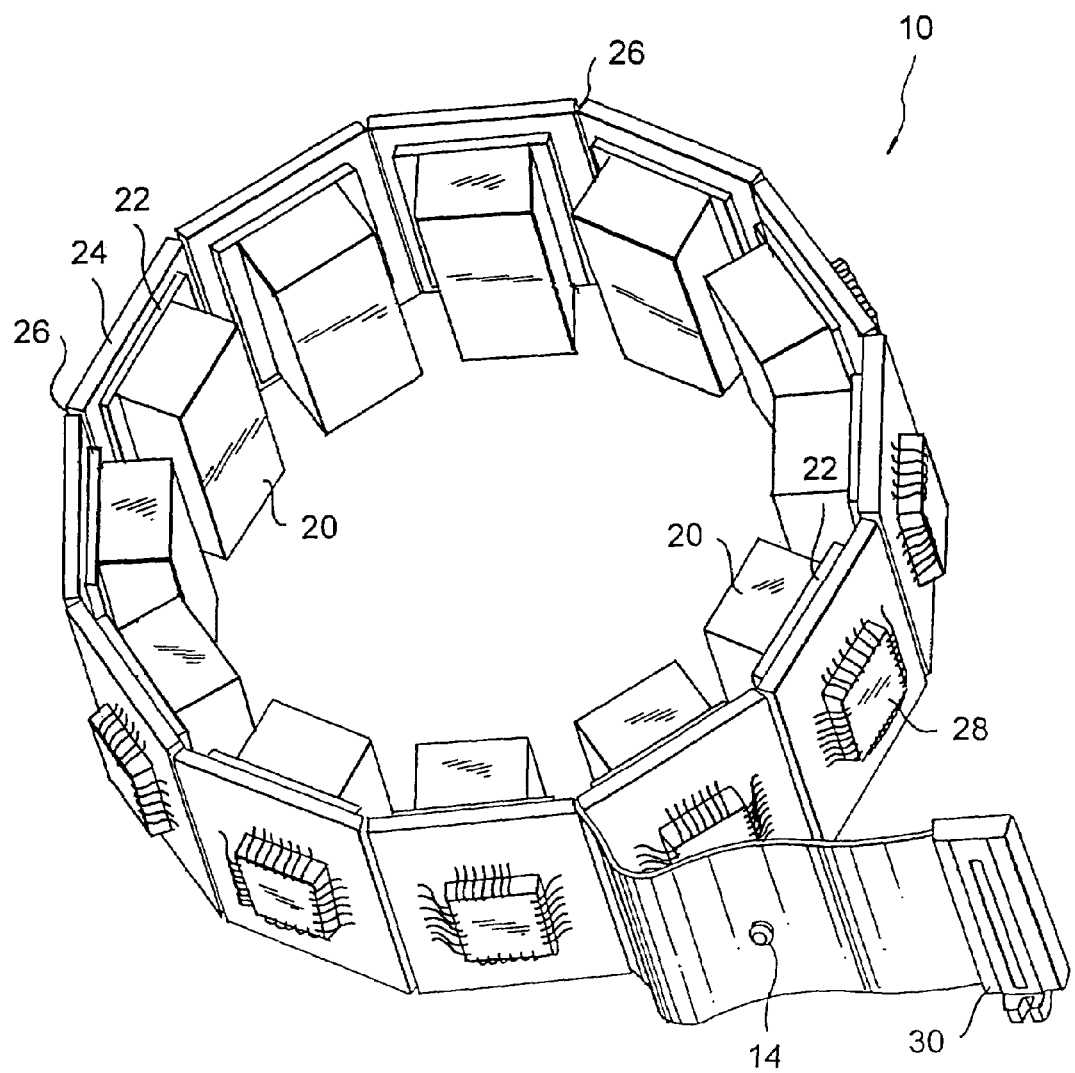
FIG. 2b is a pictorial view of an alternative embodiment of the wrist detector formed in accordance with the present invention.

As shown in FIG. 2a, the wrist detector 10 formed in accordance with the present invention preferably includes two (2) LSO crystal arrays 20 and two (2) APD detector arrays 22, although any number of LSO arrays 20 and corresponding APD detector arrays, such as twelve (12) of each as shown in FIG. 2b, is intended to be within the scope of the present invention. The wrist detector 10 shown in FIG. 2b may be used to provide three-dimensional imaging of a portion of the human body including but not limited to the wrist.

Each LSO crystal array 20 preferably includes thirty-two (32) LSO crystals configured as a 4×8 array. Each crystal is preferably about $2 \times 2 \times 10$ mm$^3$ and is coupled to a corresponding APD detector element, an array of which is available from Hamamatsu Corporation, Bridgewater, N.J. 08807 as part number S8550. The LSO crystal arrays 20 and APD detector arrays 22 are preferably mounted together in a one-to-one configuration using a thin layer of silicone room temperature vulcanizing rubber adhesive or RTV.

As shown in FIGS. 2a and 2b, the APD detector arrays 22 are preferably mounted on rigid Printed Circuit Boards (PCB) 24, which are coupled to each other by flex cable 26. Gamma radiation emitted by an annihilation event is first detected by crystals in the LSO crystal arrays 20, which translate the gamma radiation into photons. The photons are then detected by corresponding elements in the APD detector arrays 22, which translate the photons into an electrical signal. The electrical signal is coupled to electronic circuitry in a corresponding Application Specific Integrated Circuit (ASIC) 28, which is preferably mounted on a corresponding (PCB) 24. Electronic signals from each of the ASICs 28 are preferably made externally available on a connector 30 through the wrist detector cable 14.

Figure 4:
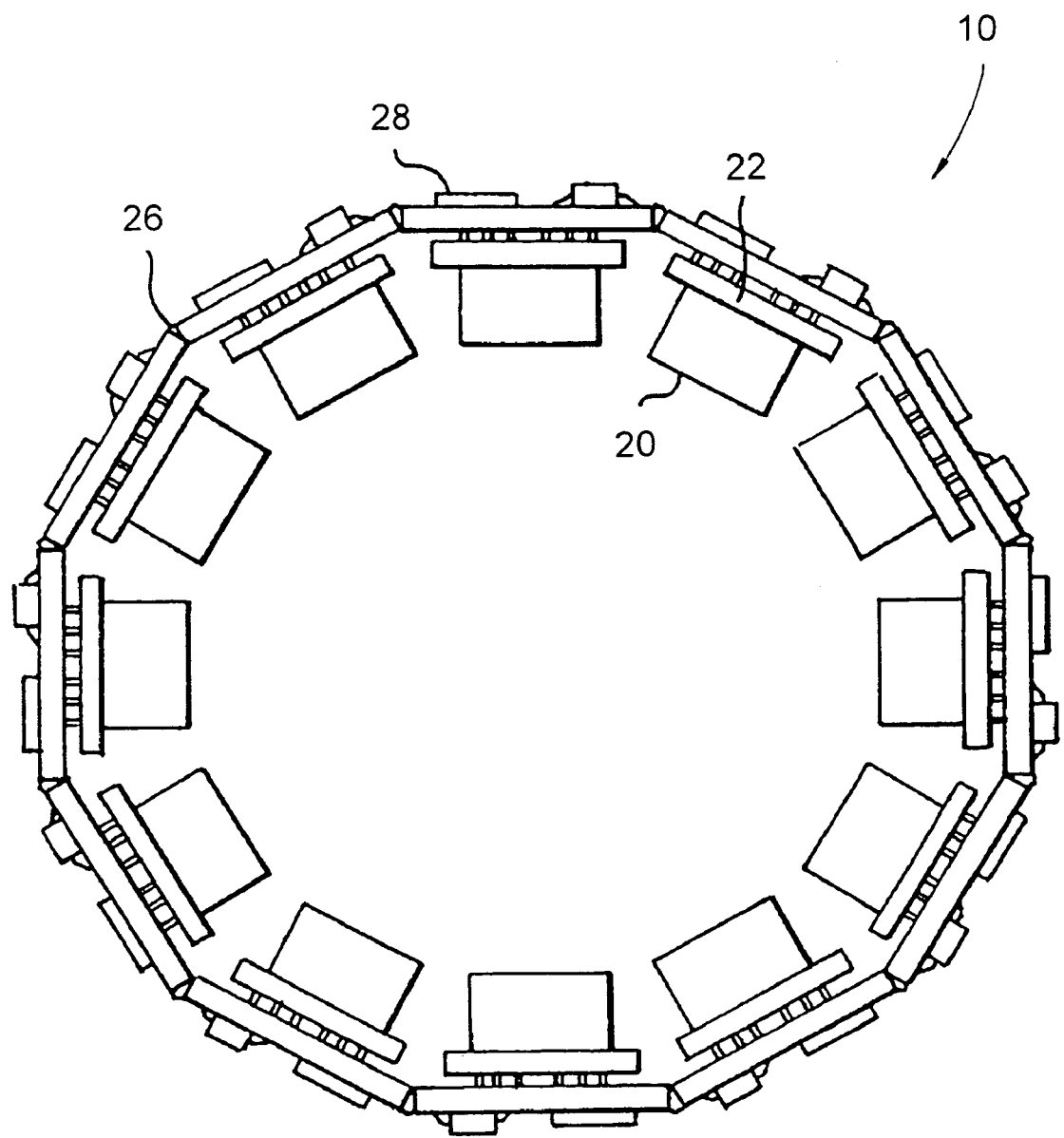
FIG. 4 is a top outline view of the alternative embodiment of the wrist detector shown in FIG. 2b.
Figure 5:
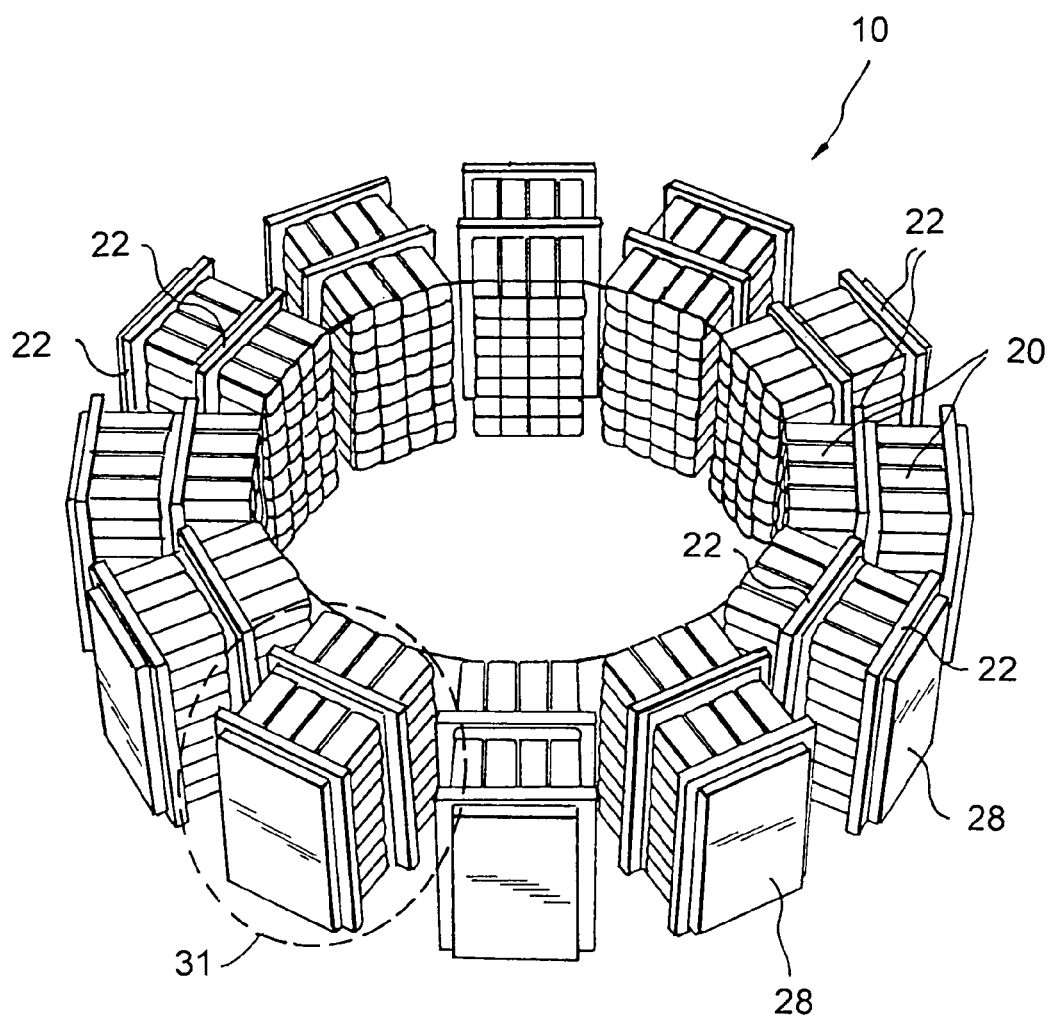
FIG. 5 is a perspective outline view of an alternative embodiment of the wrist detector formed in accordance with the present invention.

FIG. 4 is a top outline view of the wrist detector 10 shown in FIG. 2b. A perspective outline view of an alternative embodiment of the wrist detector 10, which includes stacked pairs of LSO crystal arrays 20 and APD detector arrays 22 in each of twelve (12) detector assembly blocks 31, is shown in FIG. 5.

Figure 6:
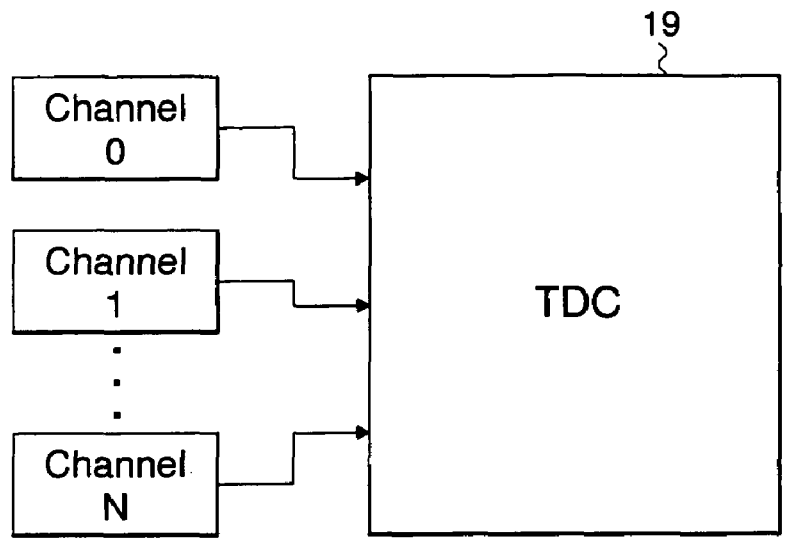
FIG. 6 is a block diagram of a conventional technique for transferring information from PET detectors for remote processing.

Time-of-occurrence information concerning an annihilation event and the corresponding address of the specific APD detector element that detected the annihilation event has conventionally been transferred to remote electronics, such as the TDC 19, for off-line processing, via separate lines. Each of these separate lines is dedicated to a single detector channel, as shown in FIG. 6. The majority of PET scanning systems include hundreds or even thousands of these channels, which render the conventional method far too cumbersome for a compact imaging system.

Figure 7:
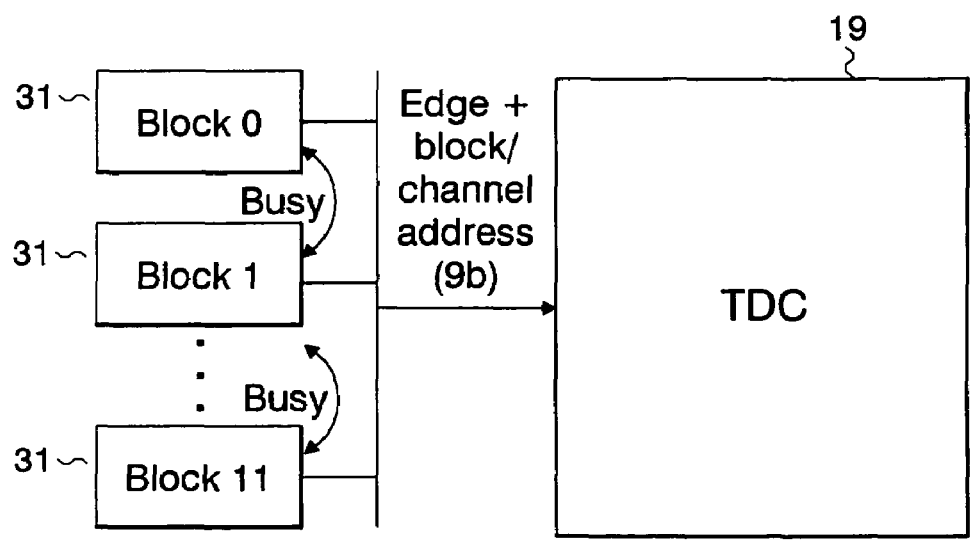
FIG. 7 is a block diagram of a technique in accordance with the present invention for serially transferring information in accordance with the present invention.

The wrist detector formed in accordance with the present invention solves this problem by using a limited number of data links to transmit information concerning multiple annihilation event from a large number of channels (N) that share the link, as shown in FIG. 7. The information required for each annihilation event is its time-of-occurrence, the address of the channel that detected the annihilation event, and the detector block corresponding to this channel. Information concerning the energy recorded in that channel may also be transmitted with the time and address information from the wrist detector in accordance with the present invention.

Figure 8:
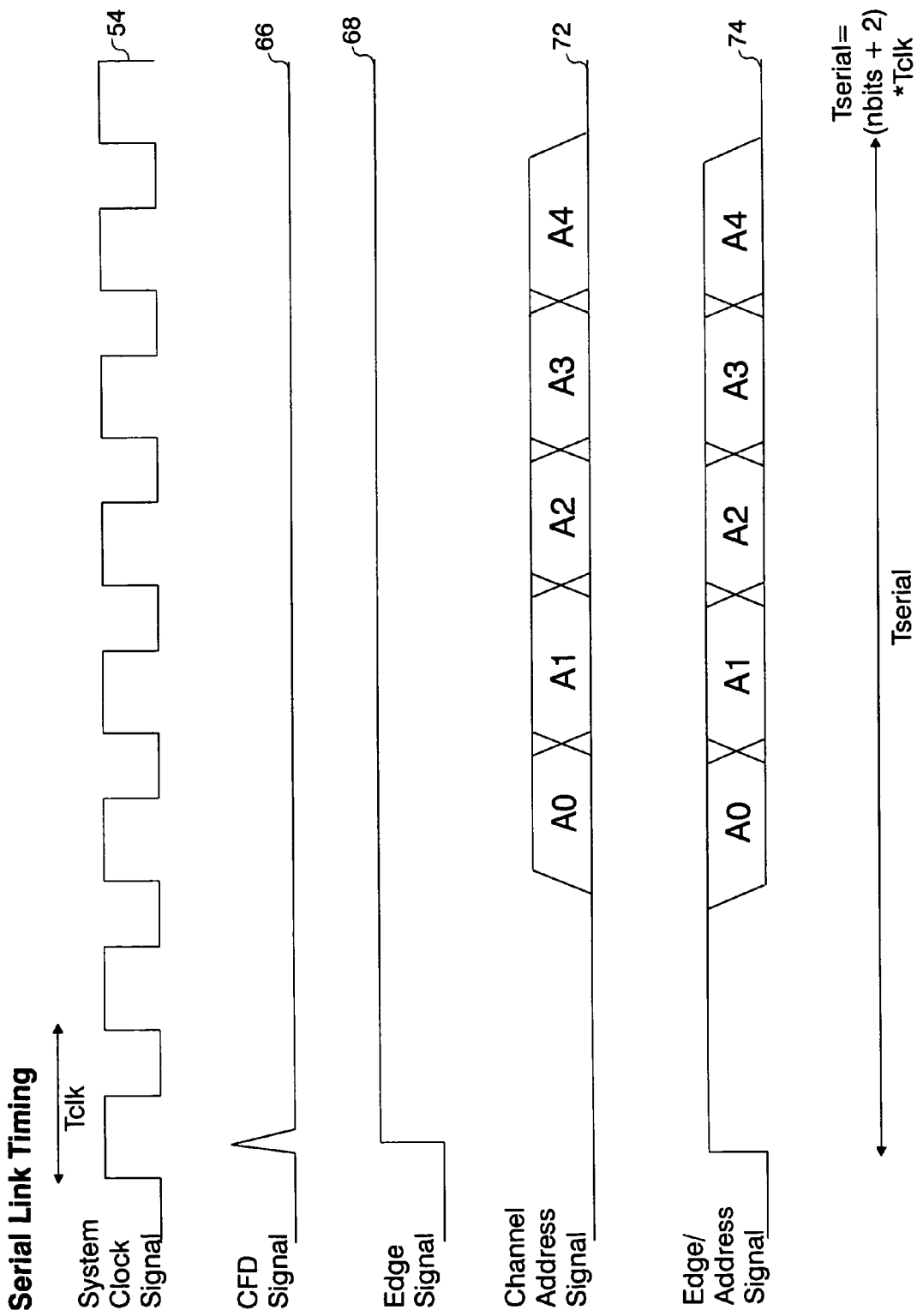
FIG. 8 is a timing diagram showing signals associated with the serial transfer of information from PET detectors in accordance with the present invention.

The time-of-occurrence of the annihilation event is preferably represented by an asynchronous position of a leading edge of a data packet from each of the ASIC devices in the wrist detector 10. The address corresponding to the channel that detected the annihilation event is preferably serially encoded in the same data packet by a digital word having a length of $\log_2(N)$ bits, where N is the number of channels in the detector block. Thus, for a detector block having thirty-two (32) channels, a minimum of five (5) bits would be required to encode the channel address. Information concerning the energy of the annihilation event is preferably encoded by the position of a second edge in the data packet. Therefore, edges representing time-of-occurrence and energy are preferably asynchronous with respect to a system clock while edges representing the channel address are preferably synchronous with respect to the system clock, as shown in FIG. 8.

Since the data link is shared between N channels, the total duration of the data packet is preferably much less than the average inter-arrival time of annihilation events in the N channels. This is preferably accomplished by increasing the frequency of the system clock. For instance, assuming no energy information is transmitted and there is one guard bit, which has a duration of one period of the system clock, between the leading edge representing the time-of-occurrence and the beginning of the channel address, the maximum duration of the data packet is preferably represented by the following equation:

$$T_{packet} = (\log_2(N)+2) * T_{clock} \quad (1),$$

where $T_{clock}$ is the period of the system clock. To prevent annihilation events from being blocked by a busy link condition the duration of the packet is preferably represented by the following equation:

$$T_{packet} << 1/(N*\text{rate}) \quad (2),$$

where rate refers to the average rate of annihilation events per channel. The busy link condition, when there is a conflict between the detection of two or more substantially simultaneous annihilation events, is preferably resolved by a priority encoder, which preferably neglects the event associated with the lower channel address.

Figure 9:
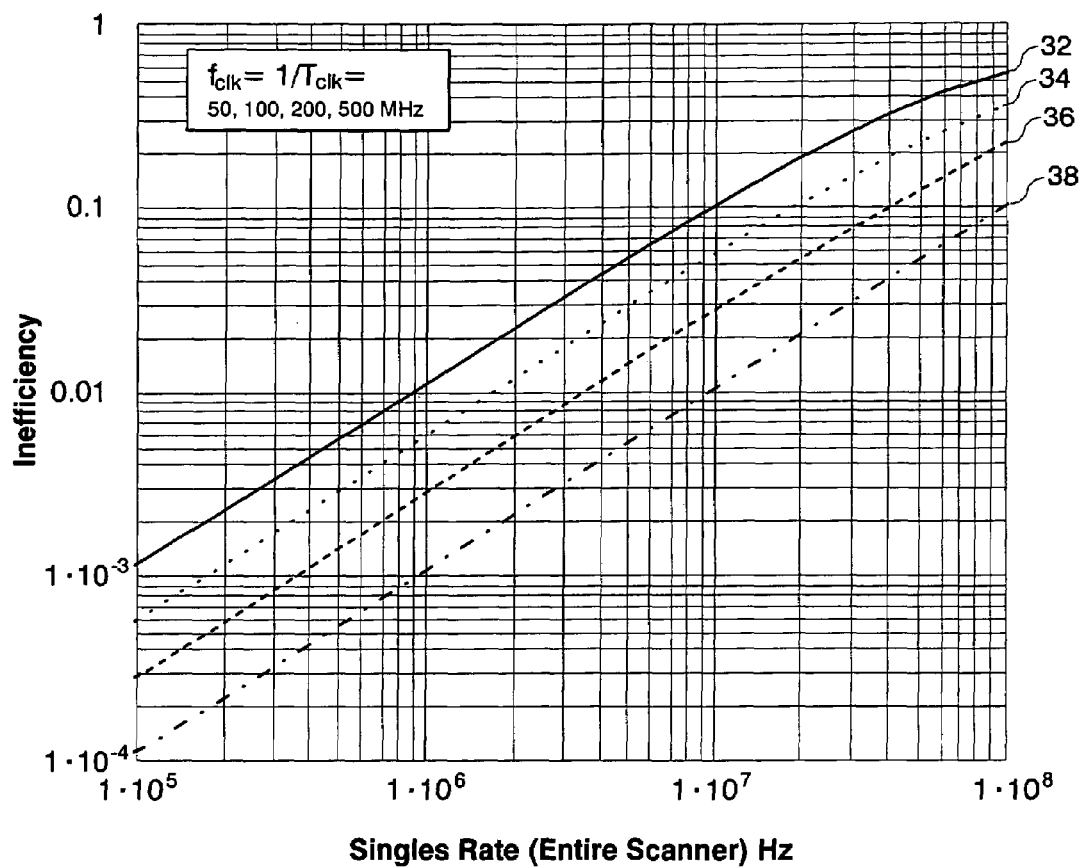
FIG. 9 is a graph of inefficiency or the probability that an event will be blocked by a busy link condition in the wrist detector formed in accordance with the present invention.

A graph showing the probability that an event will be blocked by a busy link condition, which is also referred to as inefficiency, is shown in FIG. 9 for the case of N=32 channels and system clock frequencies of 50, 100, 200, and 500 MHz as indicated by lines 32, 34, 36, and 38, respectively. The abscissa of the graph is the singles rate for the entire scanner, which is assumed to have 384 total channels organized in twelve (12) blocks of thirty-two (32) channels.

Figure 10:
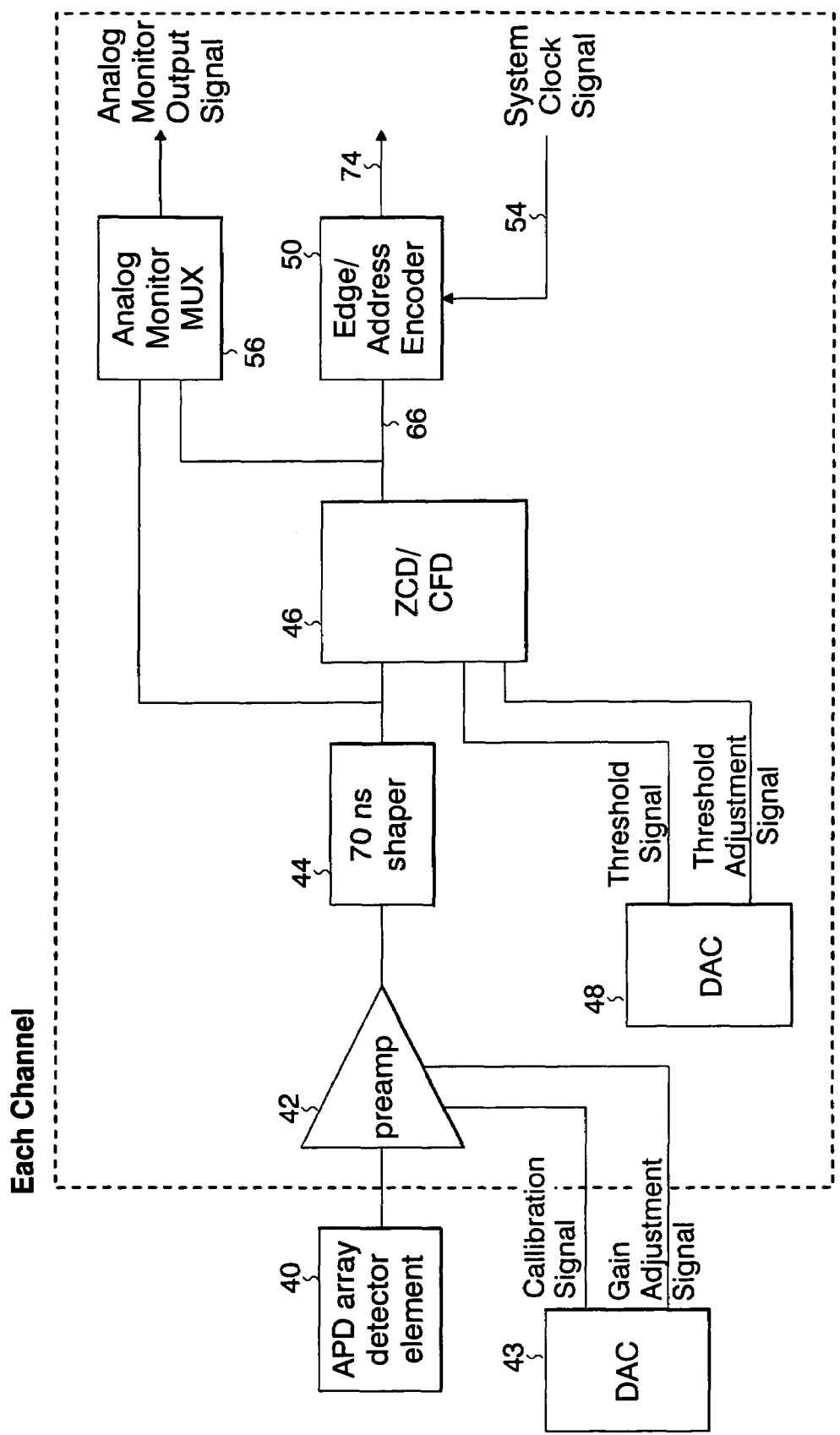
FIG. 10 is a block diagram of a preferred embodiment of the circuitry associated with detector channels in the wrist detector formed in accordance with the present invention.

FIG. 10 is a block diagram of a preferred embodiment of electronic circuitry corresponding to the channels of the wrist detector 10 formed in accordance with the present invention. The output of an element 40 of the APD detector array is preferably connected to a preamplifier 42, which inputs gain adjustment and calibration signals obtained from a digital-to-analog converter (DAC) 43. The output of the preamplifier 42 is preferably shaped to be about a 70 ns pulse by one or more filtering networks in a shaper network 44. The shaped pulse is preferably inputted to a Zero Crossing Detector (ZCD) or Constant Fraction Discriminator (CFD) circuit 46, which generates precise logic pulses in response to the shaped pulse input crossing a given threshold, as well as the peak of the shaped pulse.

Detection of the peak of the shaped pulse preferably yields a timing pulse from the ZCD/CFD 46 that represents a time-of-occurrence of the corresponding annihilation event. The time between the first threshold crossing of the shaped pulse and the second threshold crossing of the shaped pulse indicates the energy of the annihilation event using a so-called "time-over-threshold method". The energy of the annihilation event is preferably represented by the position of an energy pulse from the ZCD/CFD 46. Since the energy measurement is being performed on the shaped pulse following the preamplifier 42 and shaper circuit 44, the value of the energy measurement is preferably calibrated to yield a more accurate result.

A DAC 48 preferably provides a threshold signal and a threshold adjustment signal to the ZCD/CFD 46. The ZCD/CFD 46 is preferably based on two comparators. One comparator is used for arming the ZCD/CFD 46 by triggering on signals having the proper energy and independently setting the threshold signal for the detector channels. The threshold is preferably set for the detector channels through a serially loaded shift register (not shown). The shift registers for each of the detector block ASICs are preferably daisy-chained and share the same data, control, and clock signals. The shift registers preferably set the detector channel DACs 43, 48 to appropriate values. The remaining comparator in the ZCD/CFD 46 is preferably used to determine the baseline crossing of the bipolar signal, which represents the energy of the annihilation event as described above.

CFDs generally use a constant fraction or percentage of the input pulse to determine the timing of the output pulse relative to the input signal. This technique is not subject to jitter, which is typically caused by varying amplitudes or rise times of the inputs, such as in leading edge discriminators. The pulse output from the ZCD/CFD 46 preferably has a standardized amplitude and a preset duration.

The output of the ZCD/CFD 46 is preferably applied to an edge/address encoder 50 that outputs a serialized edge/address signal 74, which includes the time-of-occurrence and the channel address corresponding to the detected annihilation event. The system clock signal 54 is preferably inputted to the edge/address/priority encoder 50 for synchronous timing. An analog monitor multiplexer 56 is preferably provided to enable external access to analog signals within the channel circuitry, such as the analog signals before and after the ZCD/CFD 46.

Figure 11:
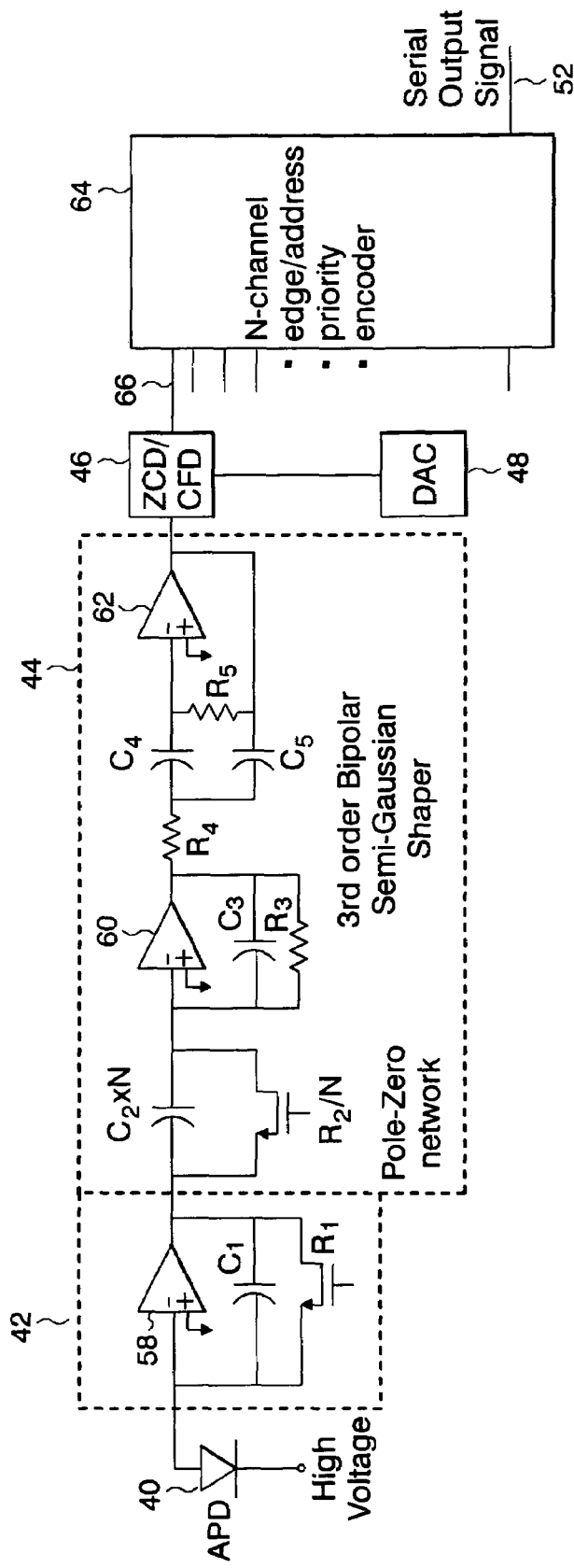
FIG. 11 is a partial schematic diagram of a preferred embodiment of front-end circuitry and a block diagram of the remaining circuitry associated with detector channels in the wrist detector formed in accordance with the present invention.

FIG. 11 is a schematic diagram of front-end circuitry in relation to subsequent functional blocks for each of the detector channels. Preamplifier and shaping network parameters are preferably optimized with respect to technological parameters and operating point characteristics of the wrist detector, such as leakage current and gain, to minimize the Equivalent Noise Charge (ENC). Simulations have predicted an ENC of about 700 electrons RMS at about a 70 ns peaking time. A gain of 3.3 mV/fC (where Cf=300 fC) was set for the preamplifier with about 1.3 mW of power dissipation.

The output of the APD element 40 is provided to the preamplifier 42 that preferably includes a parallel connection of a capacitor C1 and a resistance R1, which are connected in parallel across an inverting terminal and an output terminal of an operational amplifier 58. The resistance R1 is preferably realized by a Field Effect Transistor (FET) and the preamplifier 42 is connected in series with the output of the APD element 40.

Figure 27:
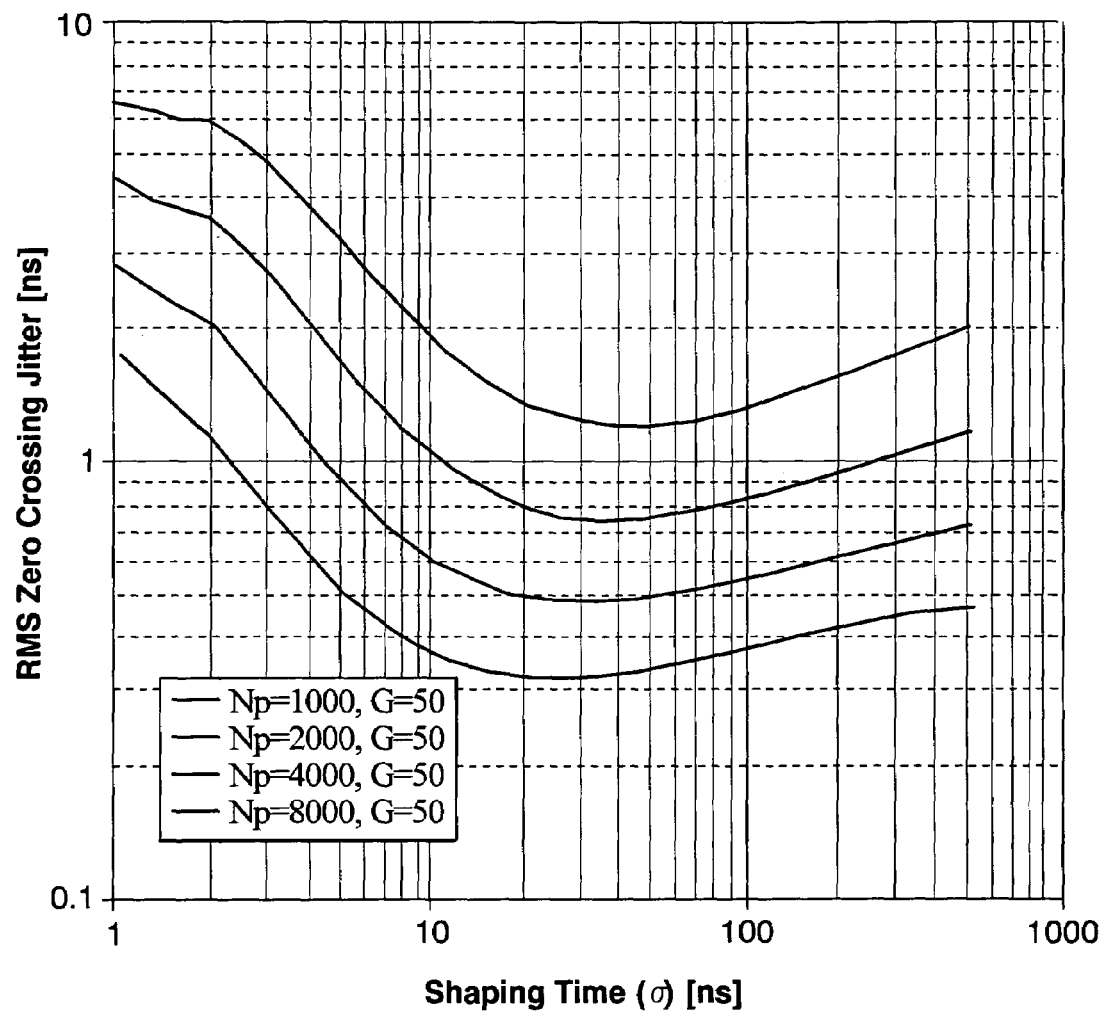
FIG. 27 is a graph representing the timing resolution or Root Mean Square (RMS) zero crossing jitter from the wrist detector formed in accordance with the present invention.

The output of the preamplifier 42 is provided to the shaper circuit 44, which preferably includes a pole-zero cancellation network, a $1^{st}$-order low pass filter, and a $2^{nd}$-order bandpass filter. An analysis was performed to determine the peaking time that optimizes timing resolution. Assuming that the LSO decay time is 40 ns and considering the series noise, the time from the peak to the zero crossing of a bipolar Gaussian between 25 ns to 90 ns would lead to a theoretical optimum of about 700 ps rms zero-crossing jitter, as indicated in FIG. 27. Therefore, the peaking time is preferably set to about 70 ns. Each transistor in the front-end circuitry is preferably optimized to minimize its electronic noise contribution.

The pole-zero network preferably includes a parallel combination of one or more capacitors C2 connected in series and one or more resistances R2 connected in series. The number of capacitors C2 is preferably equal to the number of resistances R2, as well as being greater than two (2). The resistance R2 is preferably realized by an FET and the pole-zero network is connected in series with the output of the preamplifier 42. The pole-zero network is preferably used to compensate the reset transistor non-linearity, as well as to reduce the noise contribution from subsequent stages.

The $1^{st}$-order shaper network preferably includes a parallel combination of a capacitor C3 and a resistor R3 connected in parallel across an inverting terminal and an output terminal of an operational amplifier 60. A resistor R4 and a capacitor C4 are preferably connected in series between an output terminal of the operational amplifier 60 and an inverting terminal of an operational amplifier 62. A capacitor C5 and a resistor R5 are preferably connected in parallel across the capacitor C4 and the resistor R5 is connected in parallel across the inverting terminal and the output of the operational amplifier 62, which is essentially the $2^{nd}$-order shaper network.

The non-inverting terminal of each of the operational amplifiers 58, 60, 62 is preferably connected to ground and an output terminal of operational amplifier 62 is provided to the ZCD/CFD 46. An N-channel edge/address/priority encoder circuit 64 is shown in FIG. 11, which preferably includes the edge/address/priority encoder circuits 50 shown in FIG. 10 for N channels in a detector block. The serial encoder circuit 64 outputs a single serial output signal 52 to the TDC. Further details concerning the front-end electronics for the detector channels are provided in U.S. Pat. No. 5,793,254, which is incorporated herein by reference.

Figure 12:
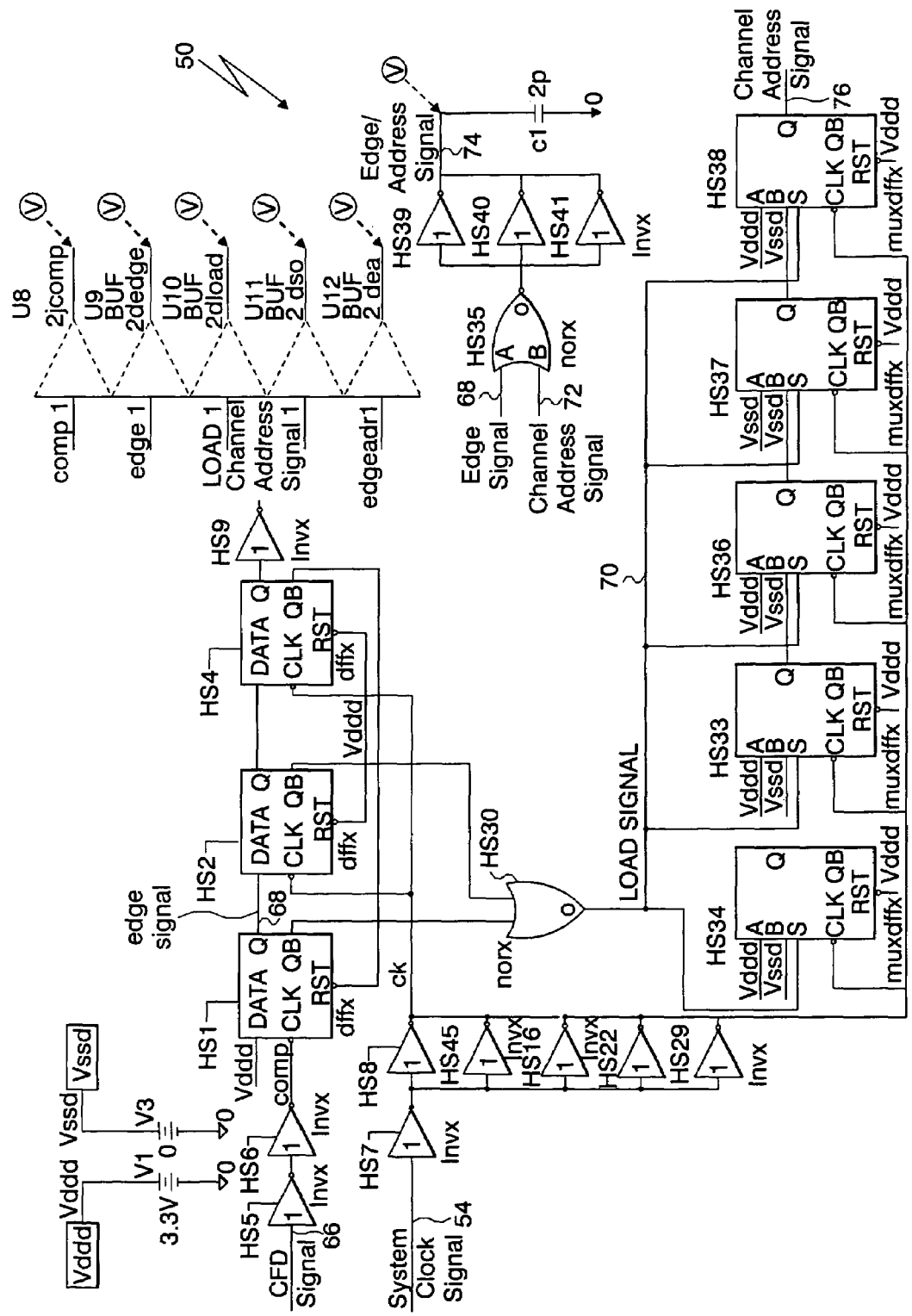
FIG. 12 is a schematic diagram of an alternative embodiment of serial encoding circuitry associated with detector channels in the wrist detector formed in accordance with the present invention.
Figure 13A:
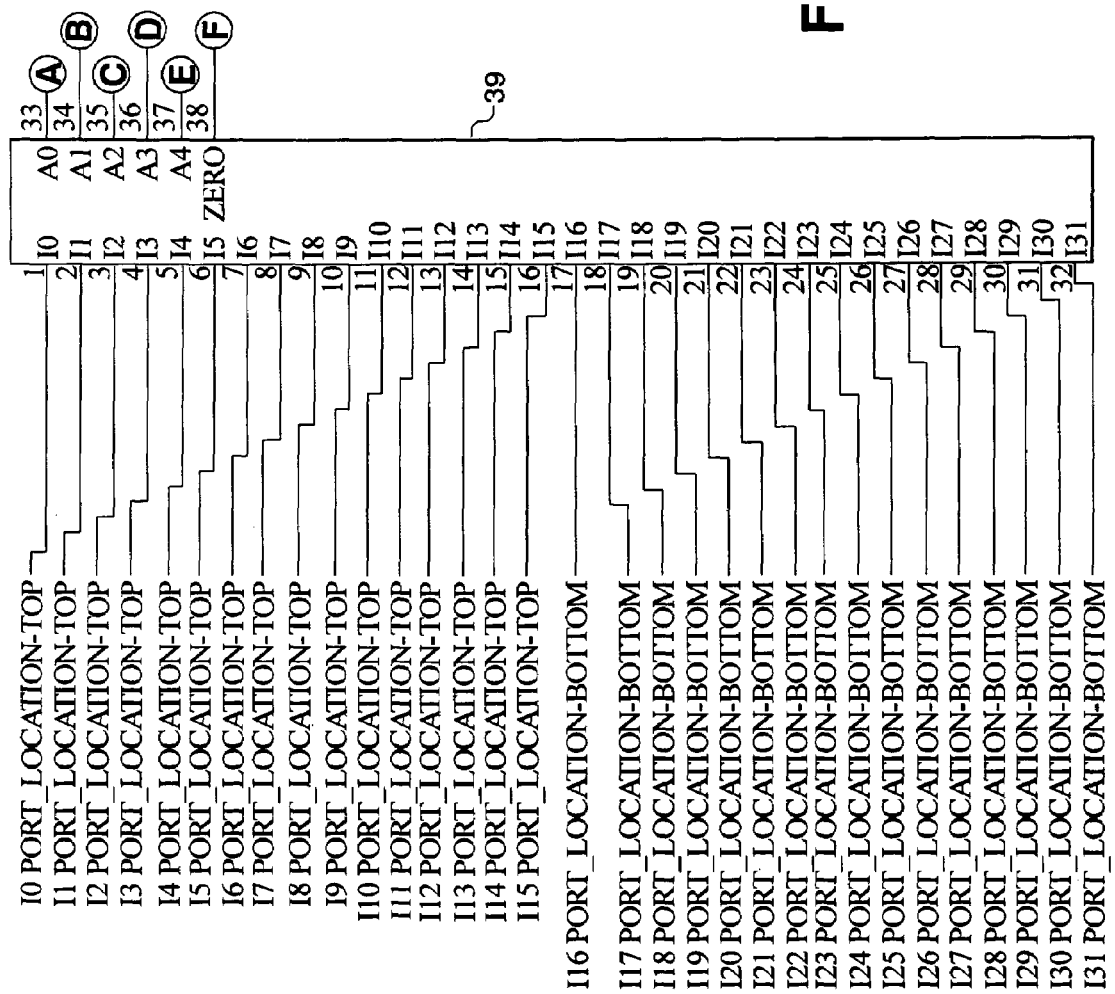
FIGS. 13–22 are schematic diagrams of an alternative embodiment of an ASIC implementation of the serial encoding circuitry formed in accordance with the present invention.
Figure 13B:
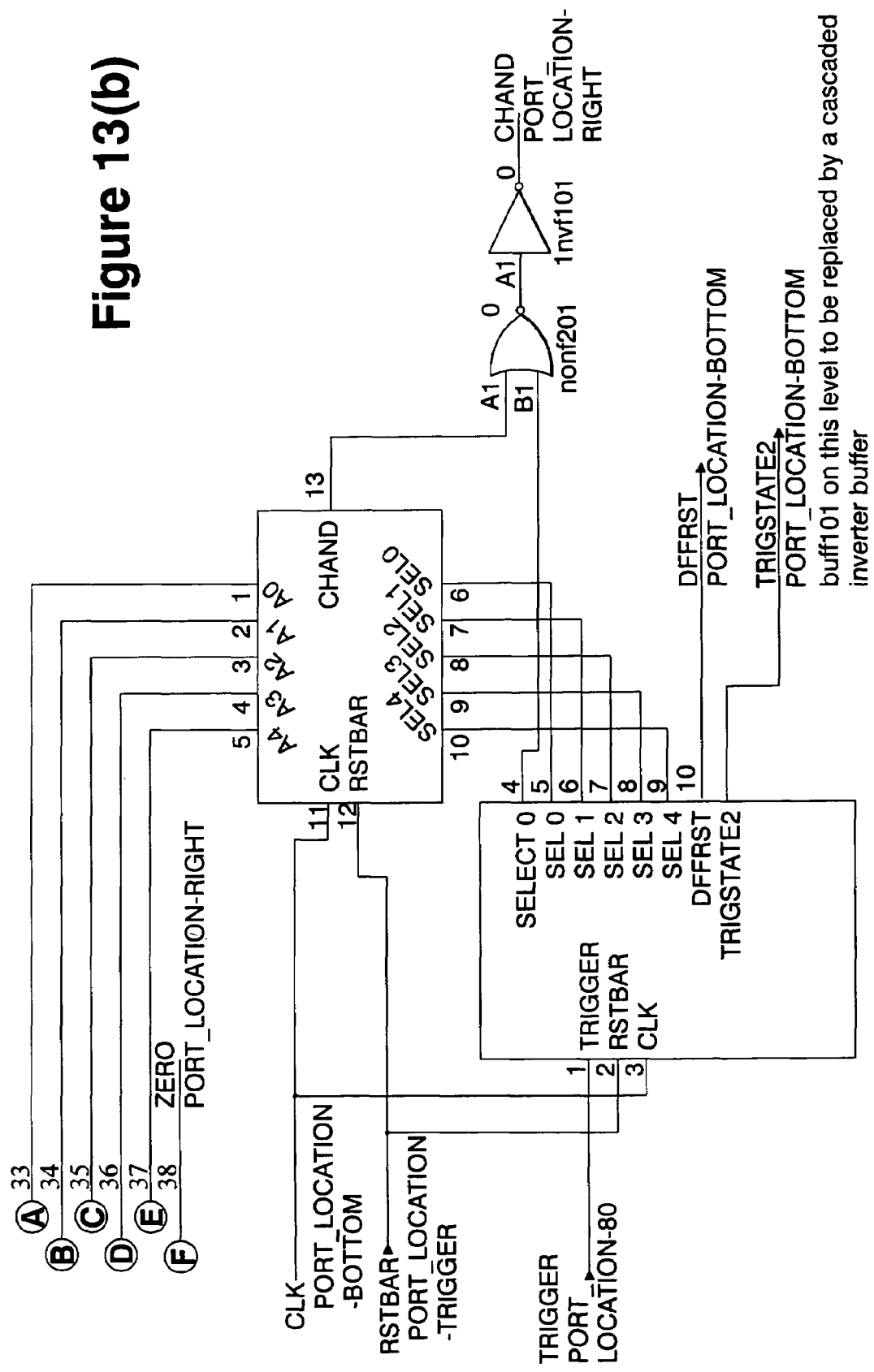
Figure 14:
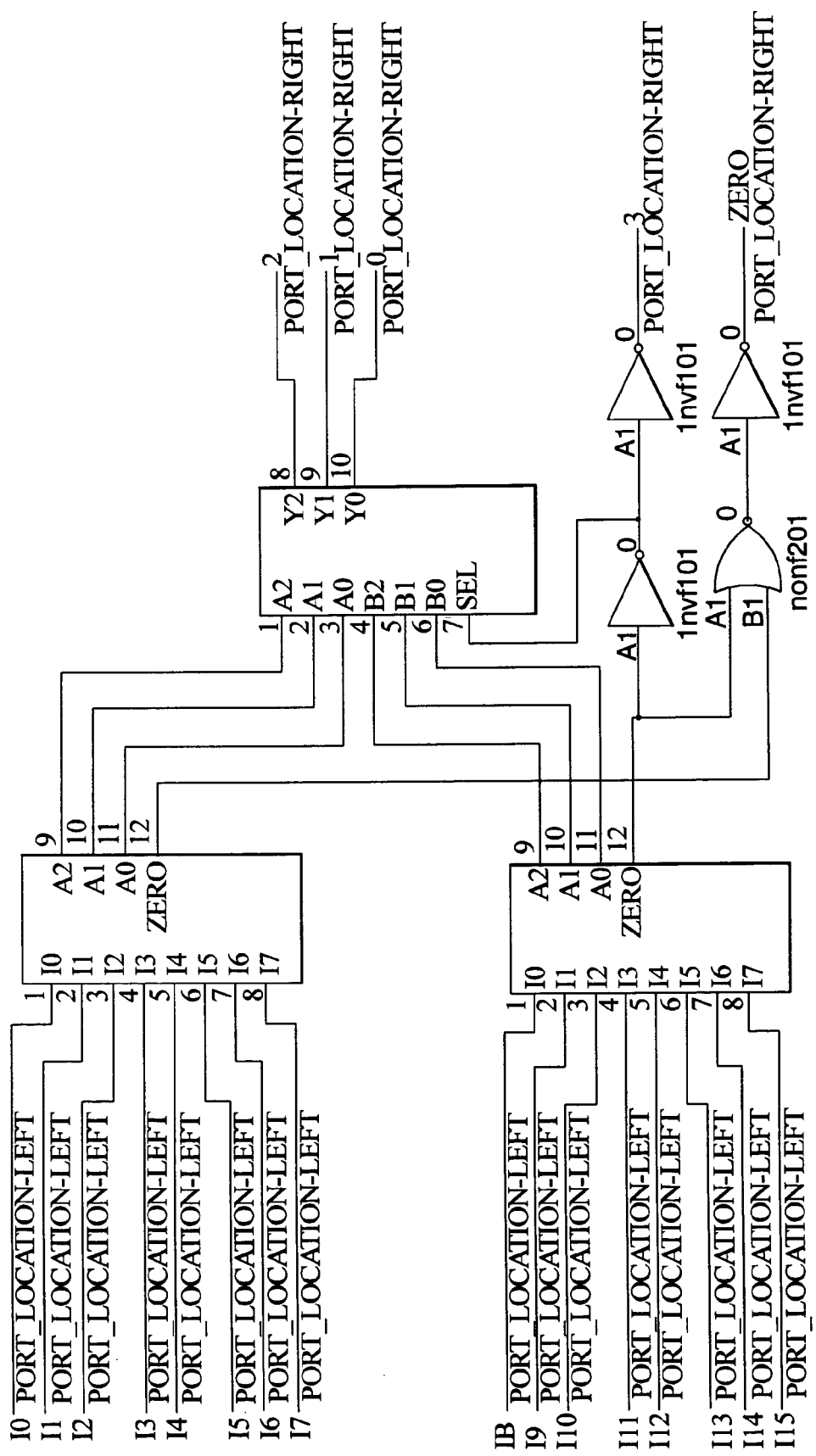
Figure 15A:
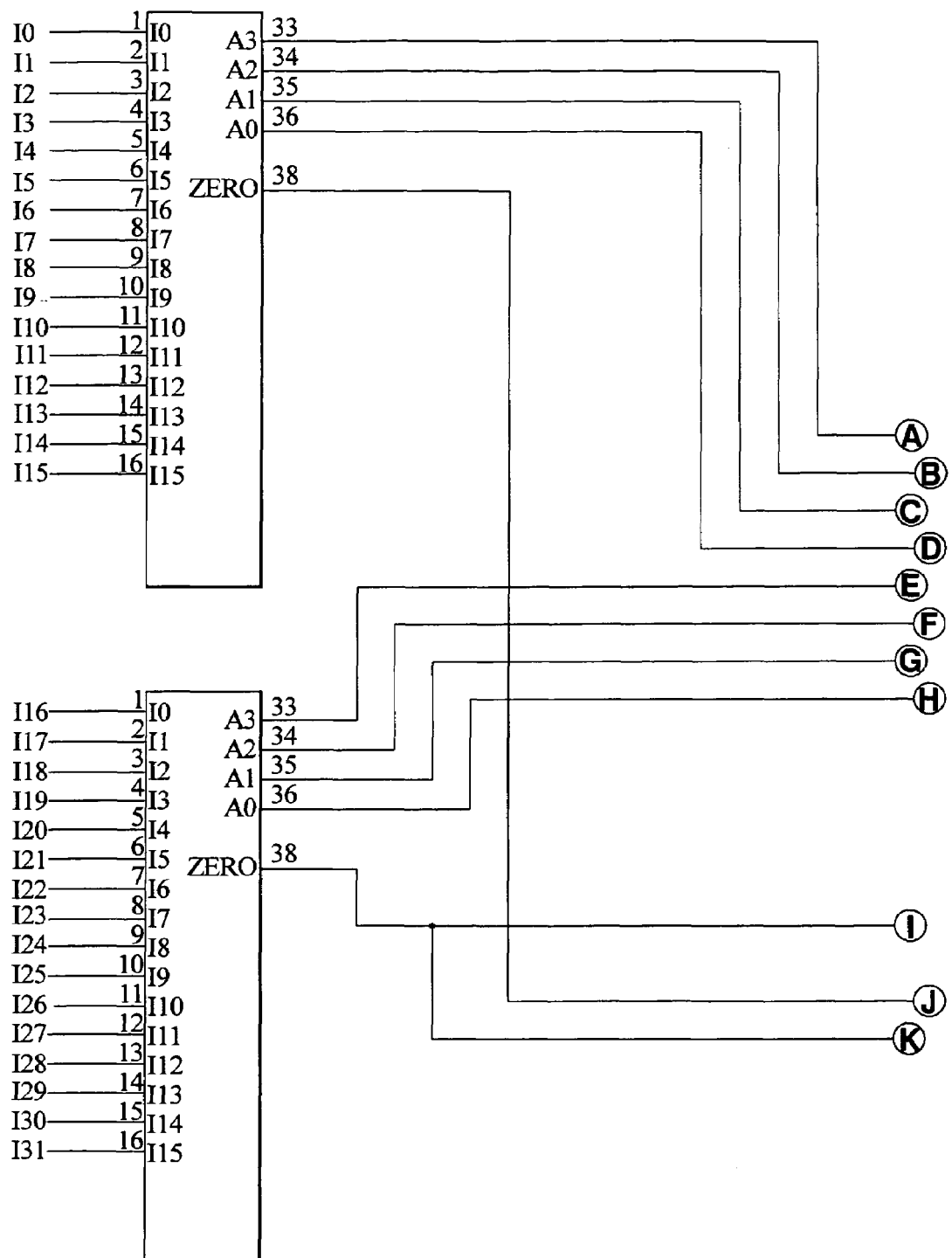
Figure 15B:
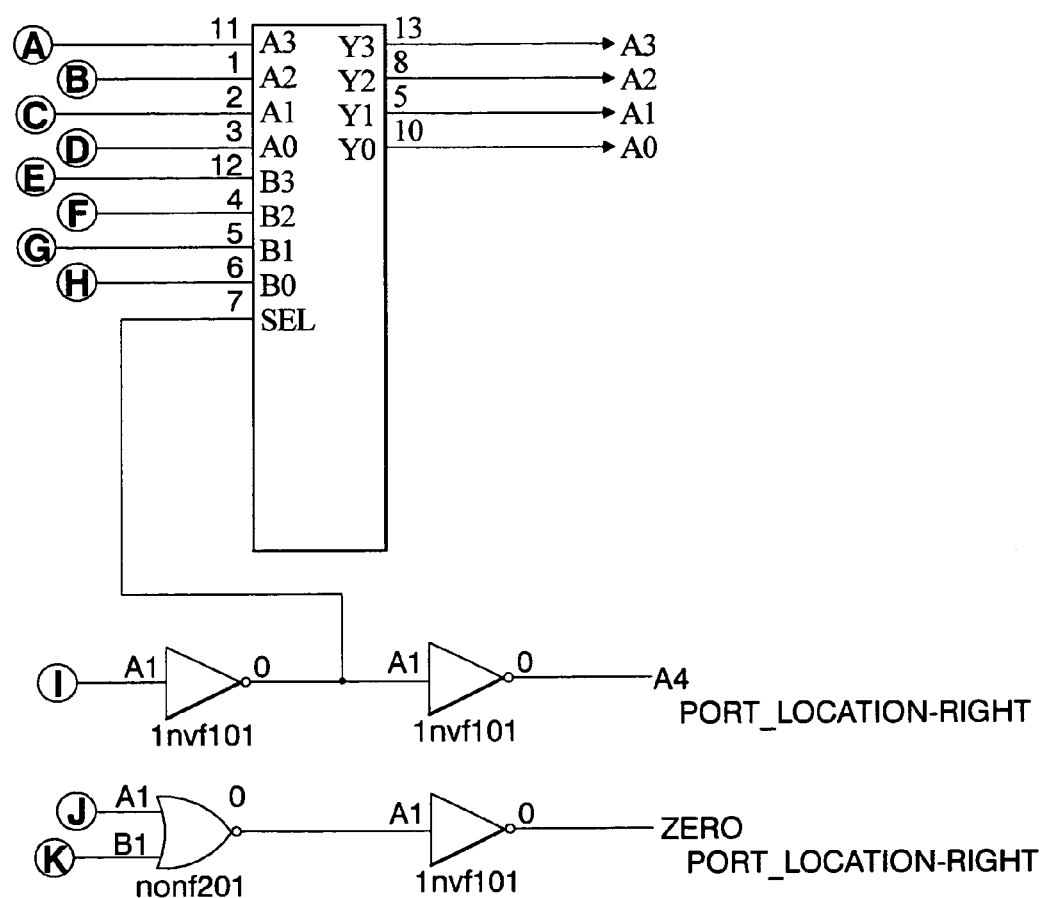
Figure 16:
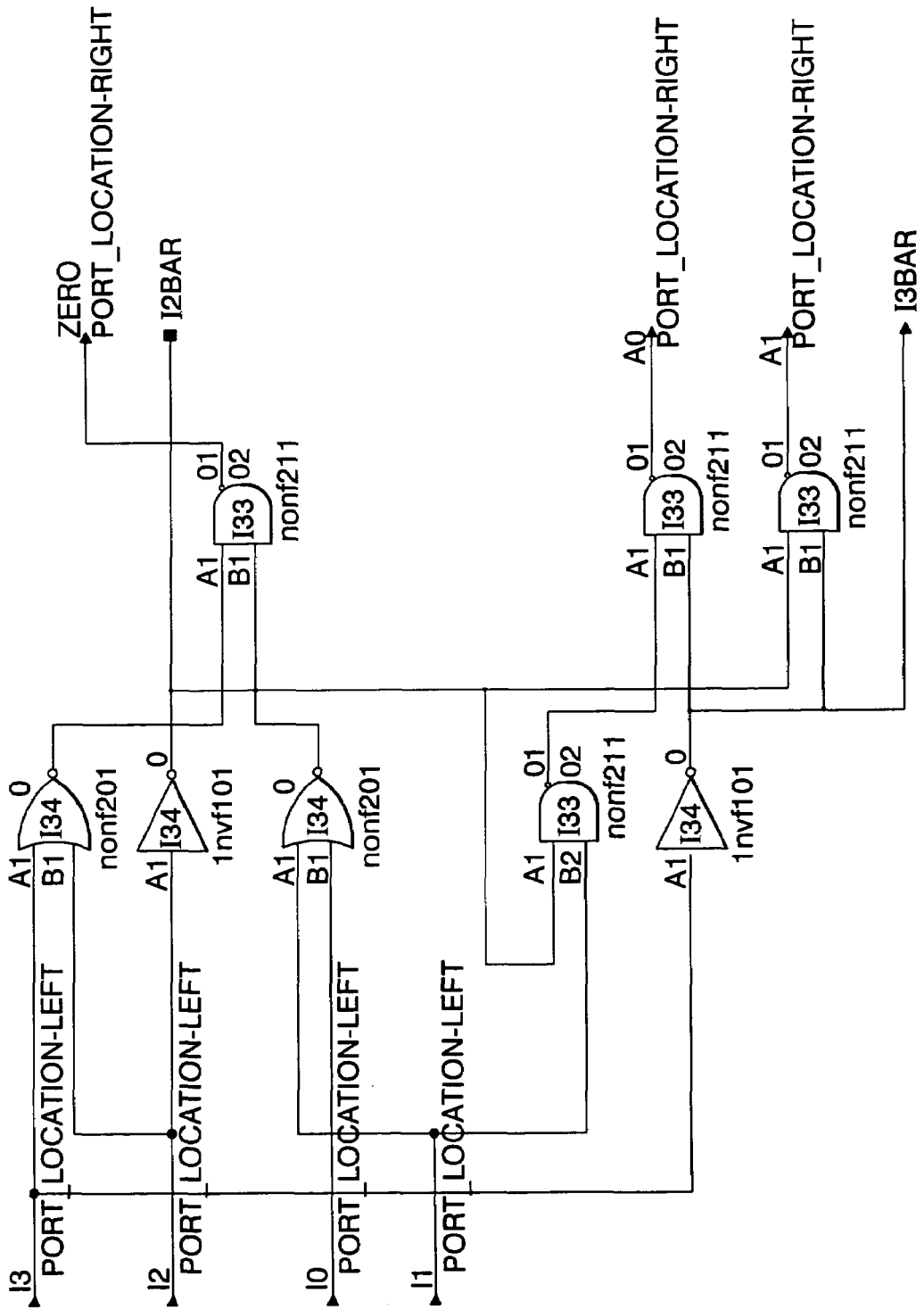
Figure 17:
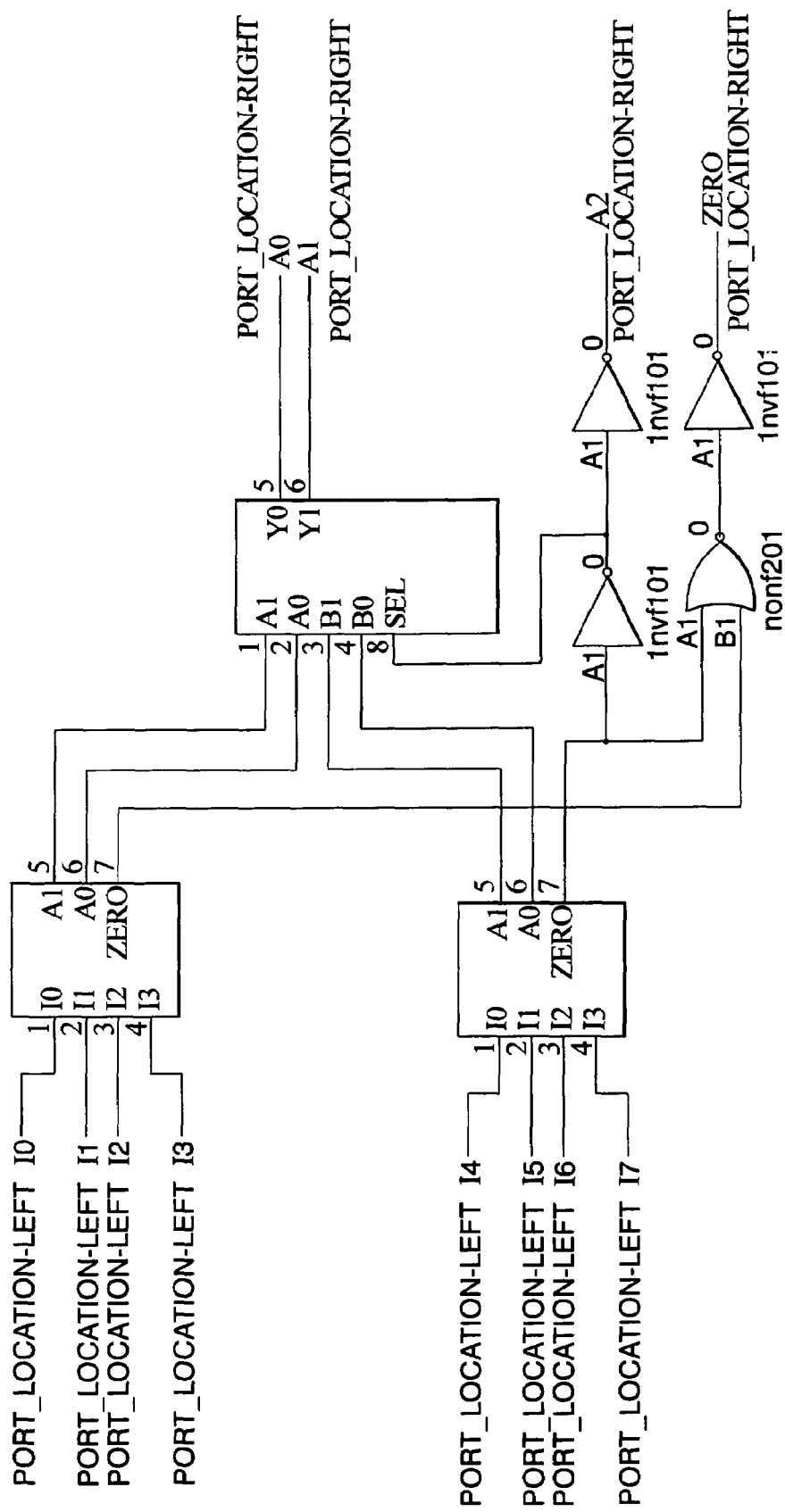
Figure 18A:
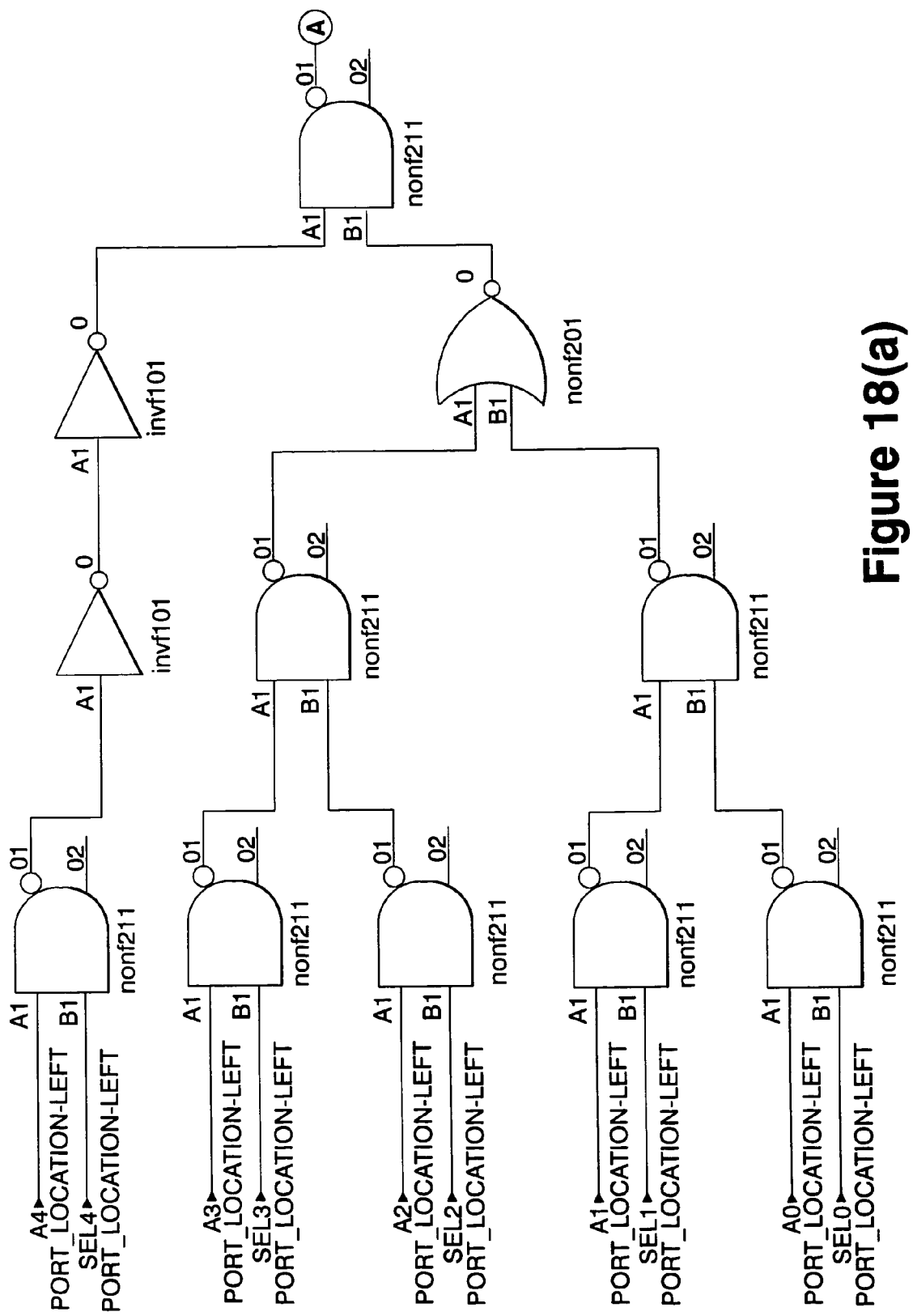
Figure 18B:
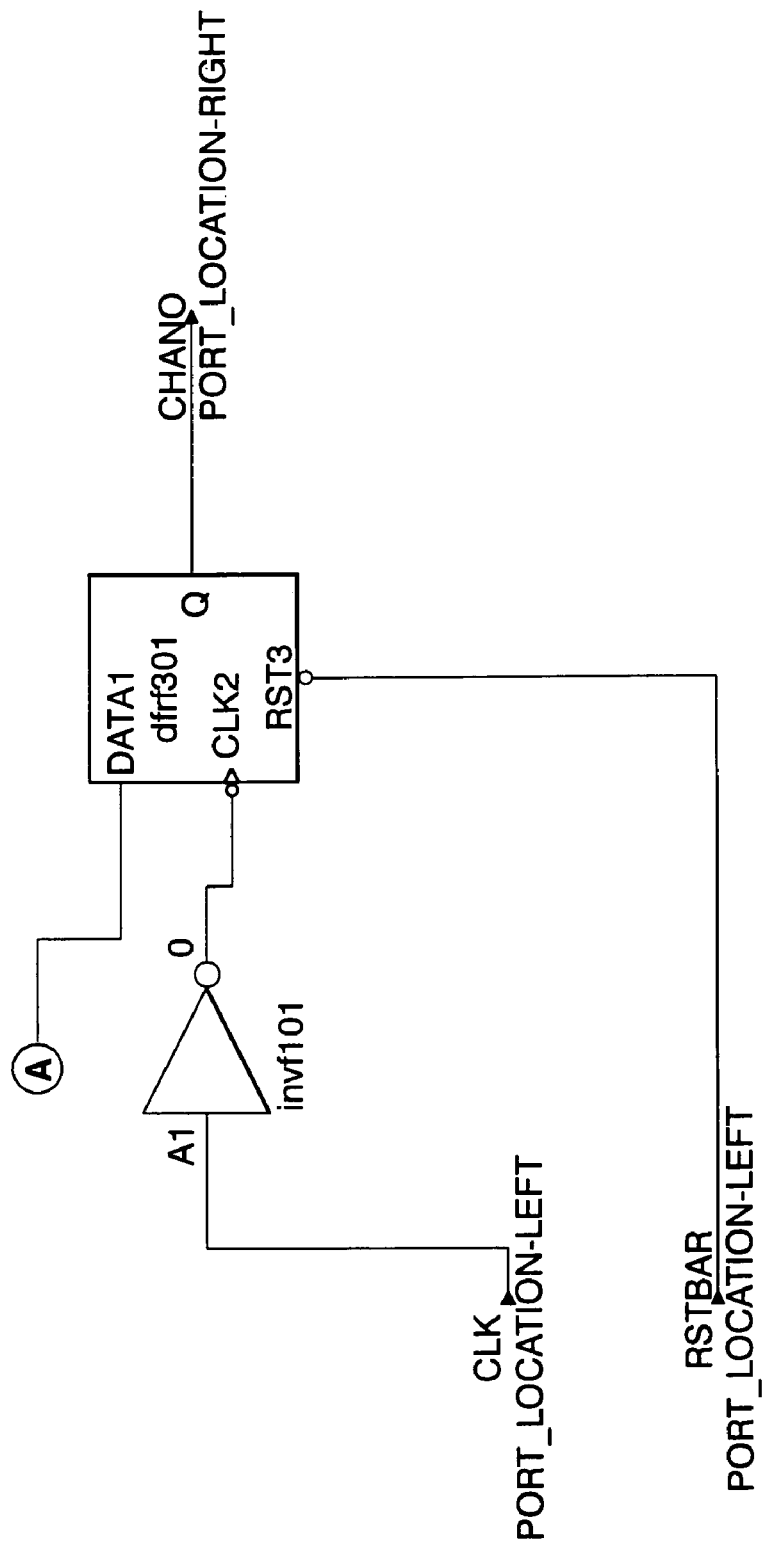
Figure 19:
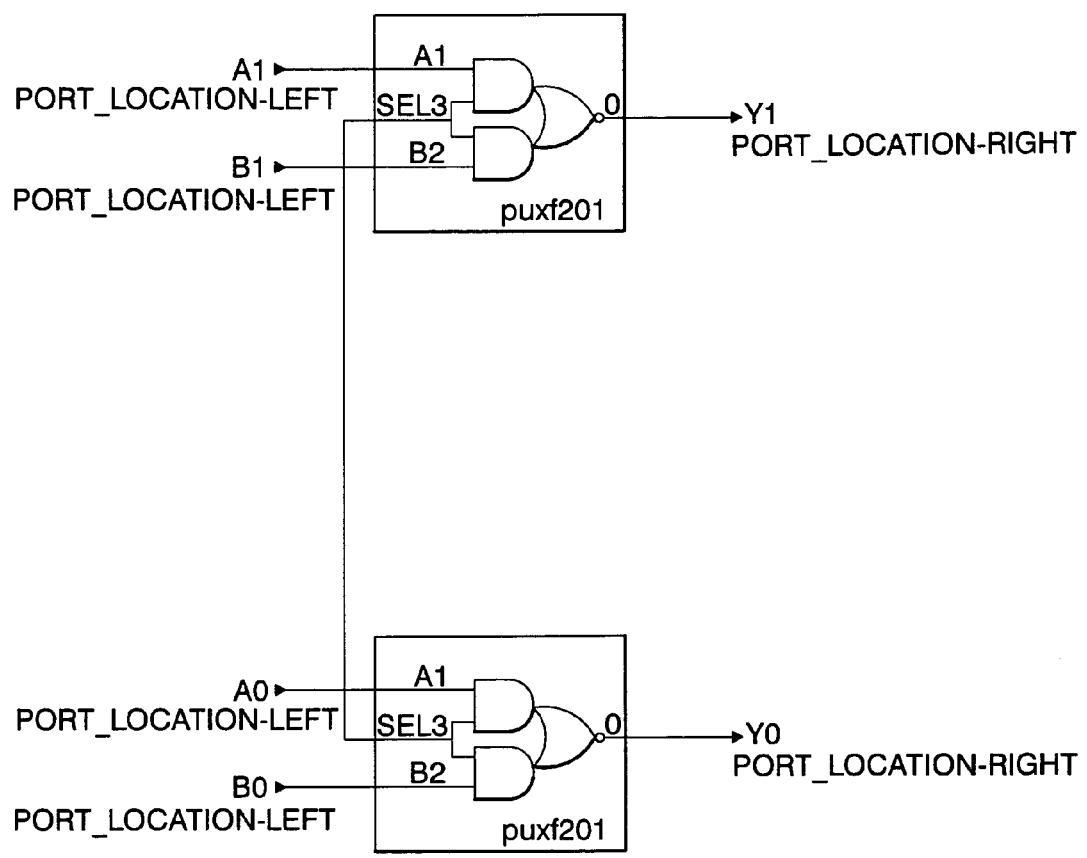
Figure 20:
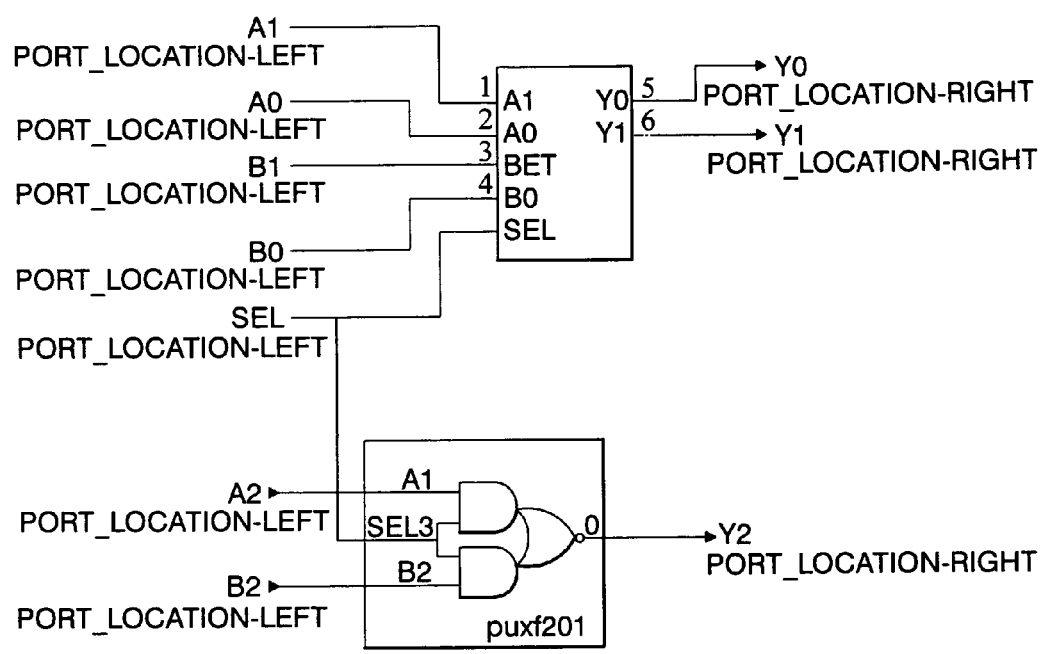
Figure 21:
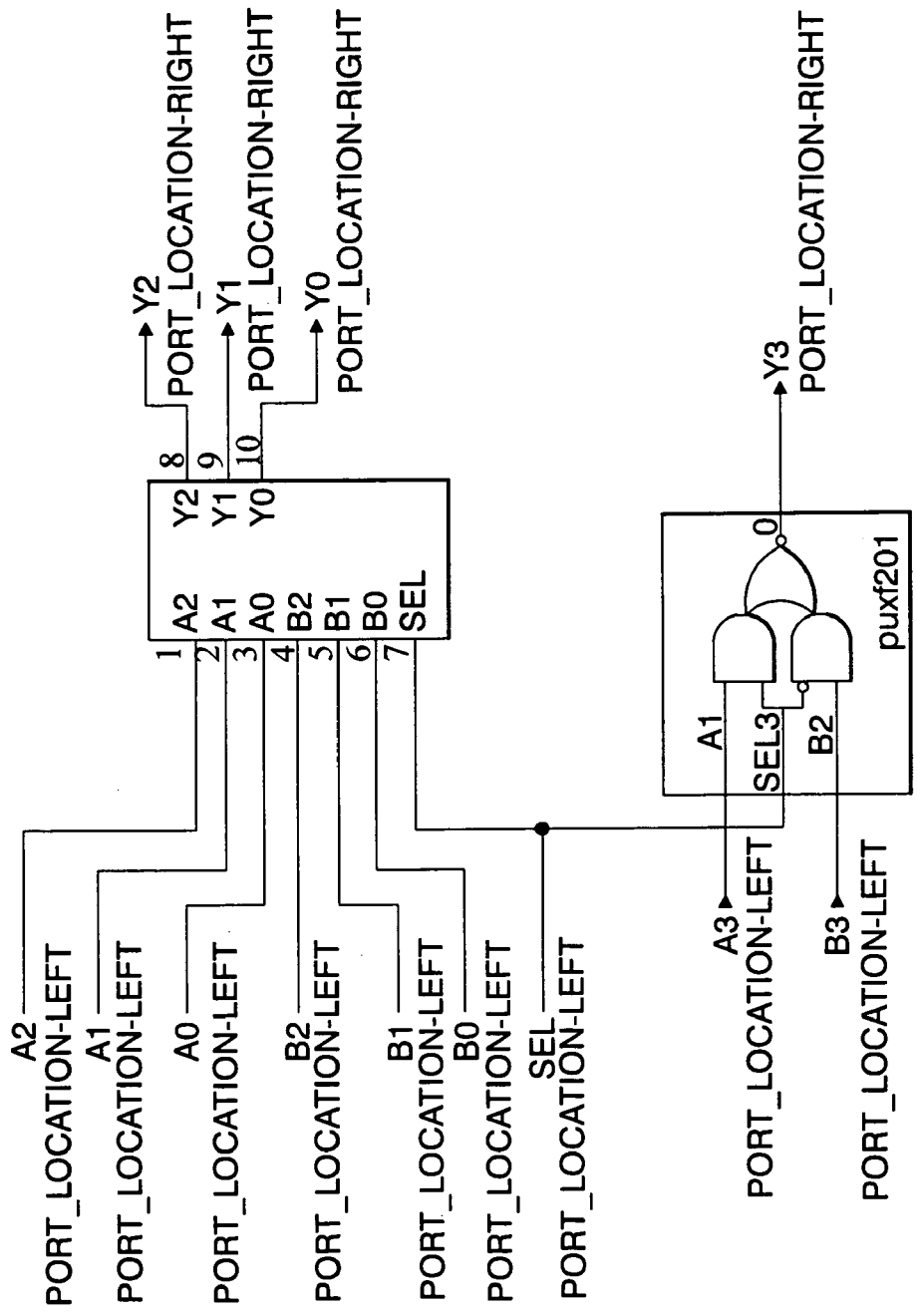
Figure 22A:
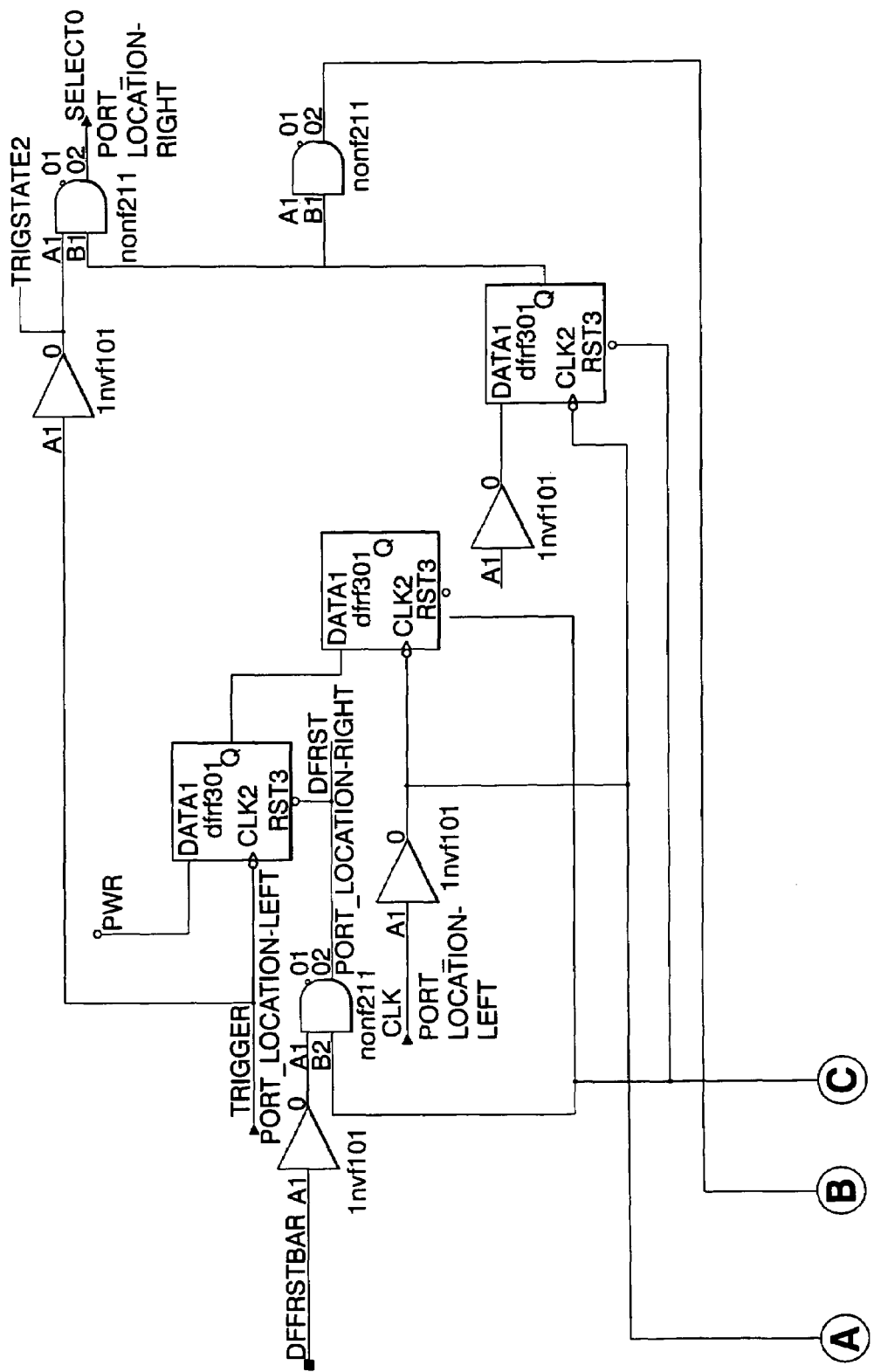
Figure 22B:
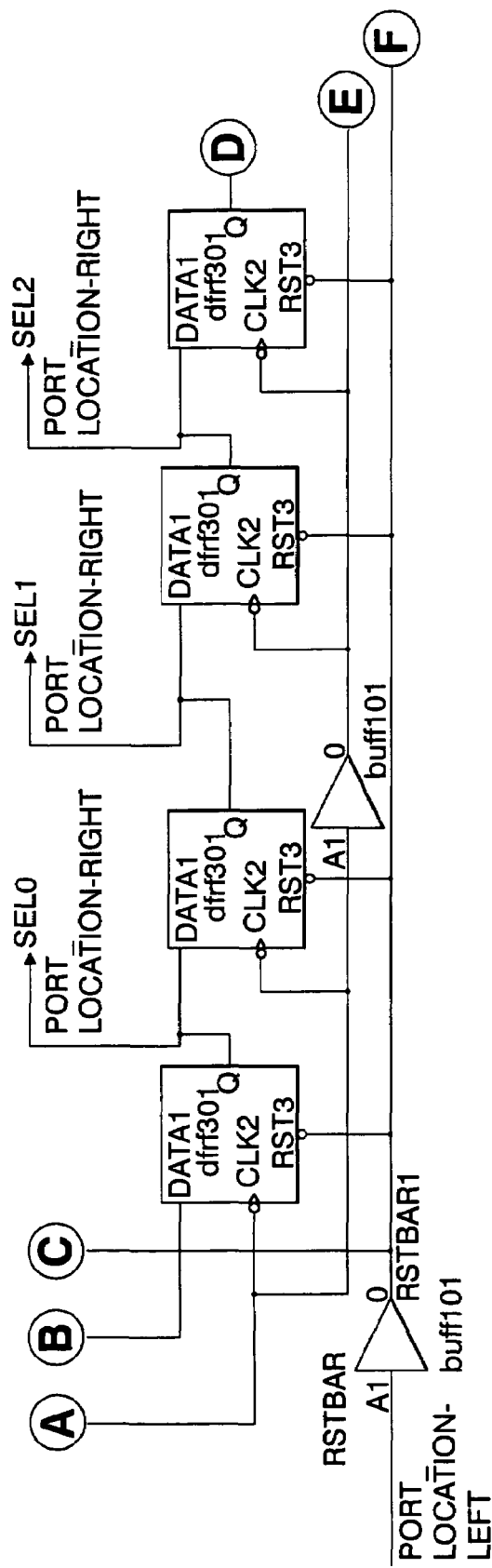
Figure 22C:
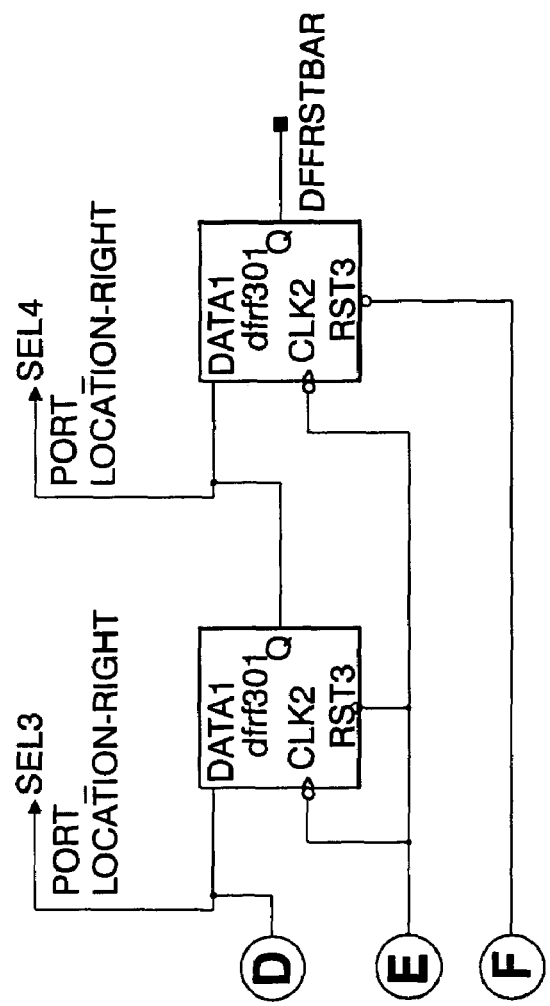

FIG. 12 is a schematic diagram showing an alternative embodiment of the edge/address encoder 50 shown in FIG. 10, which may be repeated for each of the detector channels. A CFD signal 66, which includes a pulse representing the time-of-occurrence of an annihilation event is applied to two (2) inverters HS5, HS6 for initial pulse shaping. The output of inverter HS6 is used to asynchronously clock a high level (Vddd) through a flip-flop HS1, which provides an edge signal 68 outputted from flip-flop HS1. The edge signal 68 is synchronously clocked through two additional flip-flops HS2, HS4 and the inverted output of flip-flop HS4 is used to reset flip-flop HS1. The inverted output of flip flop HS2 and the inverted output of flip flop HS1 are applied to the inputs of a nor gate HS30, the output of which is used as a load signal 70 for a shift register (HS34, HS33, HS36, HS37, HS38).

In the embodiment shown in FIG. 12 the channel address is provided as a 5-bit digital quantity. Each of the A inputs of multiplexed flip flops HS34, HS33, HS36, HS37, HS38 is connected to a high level (Vddd) or a low level (Vssd) to represent corresponding bits of the channel address. For instance, if the channel address is defined by bits A0–A4 (A0 being the least significant bit) then a binary channel address of 11101 is represented by connecting the A input of flip flop HS37 to a low level and connecting the A inputs of the remaining flip flops HS34, HS33, HS36, HS38 to a high level, as shown in FIG. 12.

The load signal 70 is an active high pulse having a duration of about one 10 period of the system clock signal 54. When the load signal 70 is high, the A inputs of each of the multiplexed flip flops HS34, HS33, HS36, HS37, HS38 are loaded into the corresponding flip flop. When the load signal 70 is low, the flip-flops HS34, HS33, HS36, HS37, HS38 function as a 5-bit serial shift register, the output of which is a channel address signal 72. The channel address signal 72 is combined with the edge signal 68 using a nor gate HS35 and inverters HS39, HS40, HS41 to yield an edge/address signal 74.

A timing diagram of these signals is provided in FIG. 8, which shows that the edge/address signal 74 is a combination of asynchronous analog information representing the time-of-occurrence of an annihilation event by the position of an edge, as well as synchronous digital information representing the address of the particular channel that detected the annihilation event. The combination of this information permits a single serial data link to be shared by each of the channels in a detector block or each of the channels in the wrist detector formed in accordance with the present invention.

FIGS. 13–22 are schematic diagrams of an alternative embodiment of the N-channel serial encoder 64 shown in FIG. 11, in which N=32. These diagrams were prepared in contemplation of an ASIC implementation of the encoder 64, which essentially incorporates the encoder circuitry shown in FIG. 12 for each of the 32 channels, as well as circuitry to combine the outputs of each of the channel encoder circuits into a single serial output signal 52 shown in FIG. 11 and a priority encoder to resolve busy link conditions. The ASIC is preferably designed to have minimal power dissipation so as not to affect the gain of the APD detector array, which is sensitive to temperature.

FIG. 12a is a schematic diagram of a preferred embodiment, which is implemented in an ASIC, of the serial encoding circuitry shown in FIG. 12. The preferred embodiment is similar to that shown in FIG. 12, except that a single shift register 67 is used to serialize the addresses for each of the channels in the ASIC. The channel address A0–A4 is preferably generated by a 32-to-5 priority encoder, such as an encoder 39 shown in FIG. 13.

An asynchronous trigger signal 71, which represents the time-of-occurrence of an annihilation event, is preferably applied to a time signal generator 73. A serializing signal 75, which is a synchronous derivative of the trigger signal 71, propagates through the shift register 67 to generate enabling signals Select0–Select4. The enabling signals Selecte0–Select4 gate successive bits of the channel address through combinatorial logic 77 to a flip flop 79 that outputs the serialized channel address signal 72.

Figure 23:
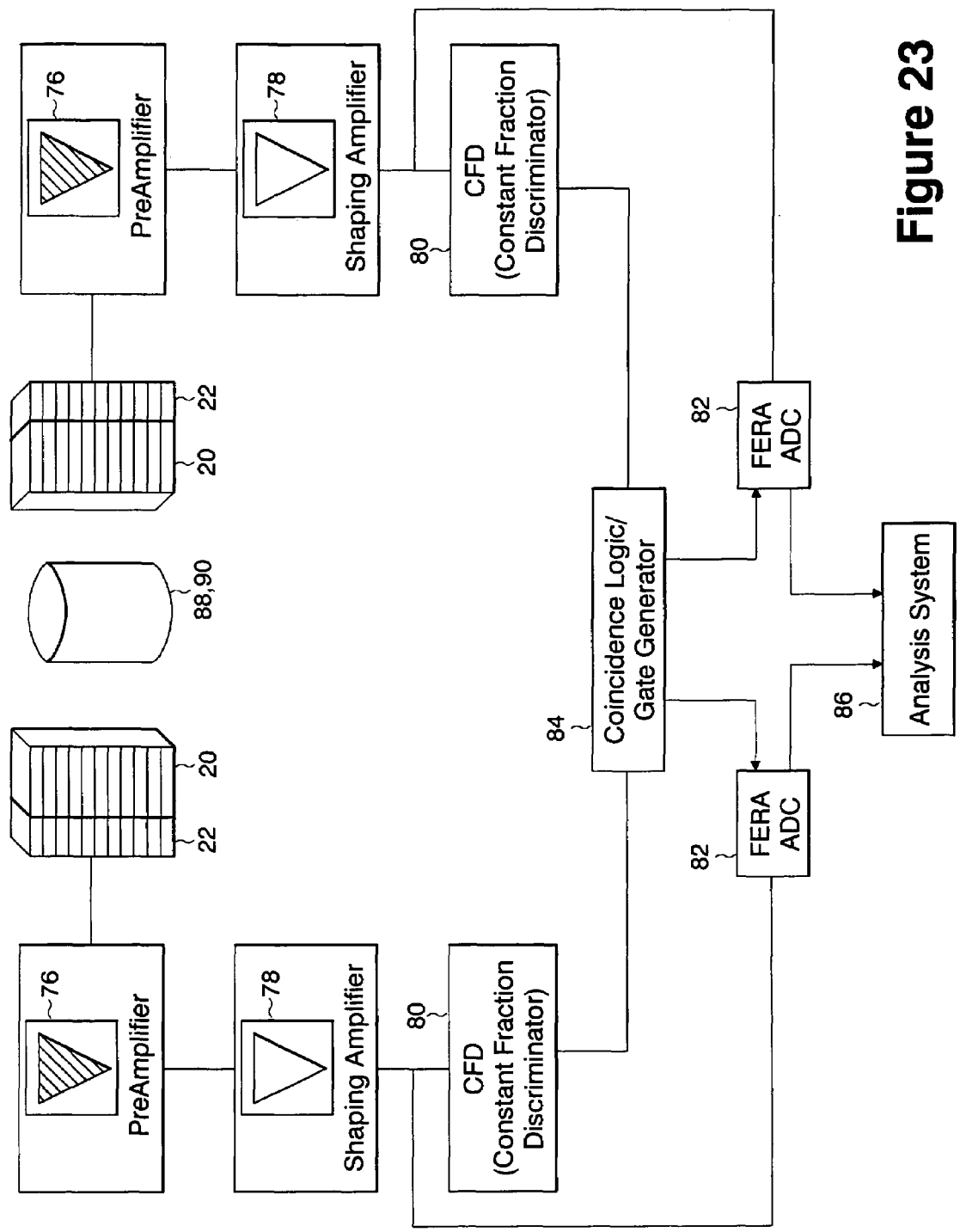
FIG. 23 is a block diagram of an experimental measurement setup for use in collecting sample data in accordance with the present invention.

In an experimental measurement setup shown in FIG. 23, which is intended to represent an alternative embodiment of the present invention, signals from the APD detector array 22 are preferably inputted into a charge sensitive preamplifier 76 and then into shaping amplifiers 78 with about a 70 ns peaking time. The output of the shaping amplifiers 78 are then preferably divided between constant fraction discriminators (CFD) 80 with about a 50 mV threshold and Computer Automated Measurement and Control Fast Encoding and Readout analog-to-digital converters (CAMAC FERA ADC) 82 that digitize these signals. A Nuclear Instrumentation Methods (NIM) logic unit or coincidence logic/gate generator 84 preferably selects coincidence events and generates a gate for the ADC's 82. Data are preferably transferred from the ADCs 82 and analyzed in an external system 86.

Sensitivity of the APD detector array 22 is preferably determined using a known level of radioactivity in a 2 mm line source. An estimate of this sensitivity is also preferably calculated for the volume of radioactivity in the field of view of the detectors 22, which is about 0.05 cm$^3$, and compared to the measured value. The measured value is about 0.10 Hz/nCi. The count rate is typically low with this sensitivity, but is preferably increased by integrating over several seconds. It should be noted that the described sensitivity relates to a single pair of detectors that are about 10 mm deep. The sensitivity is preferably enhanced by increasing the quantity of detectors in the array and/or the depth of the LSO crystal arrays 20.

An energy resolution study is preferably performed using the APD detector array 22. The energy resolution is preferably sufficient to clearly delineate a 511 keV signal from the background. LSO crystal arrays 20, which are available from Proteus, Inc., Chagrin Falls, Ohio 44022 and CTI, Inc., Knoxville, Tennessee 37932, are preferably used in the experiment.

LSO crystal arrays 20 available from CTI provide a signal of about 2500 primary photoelectrons per MeV and an energy resolution of about 23% Full Width Half Maximum (FWHM) for 511 keV gamma rays. Two configurations were tested using the LSO crystal arrays 20 available from Proteus, each having a reflective barrier between the elements, which has excellent reflective properties and improves energy resolution. In one configuration, the reflector was bonded to the crystal surfaces, and in the other, it was not.

The bonded array provides about 2300 primary photoelectrons per MeV and an improved energy resolution of about 17%, while the unbonded surface provides about 2600 primary photoelectrons per MeV and an energy resolution of about 13%. The APD array 22 provides an average gain of about 50, which results in a signal-to-noise ratio of at least 50:1. Differences in the gain of individual channels caused a shift in the associated pulse height spectra. These differences are preferably compensated for by shifting the peak position of the photopeak in each channel to the average peak position of the thirty-two (32) channels in each array. This makes it more convenient to set a threshold such that only photopeak events are used for image reconstruction.

Figure 24:
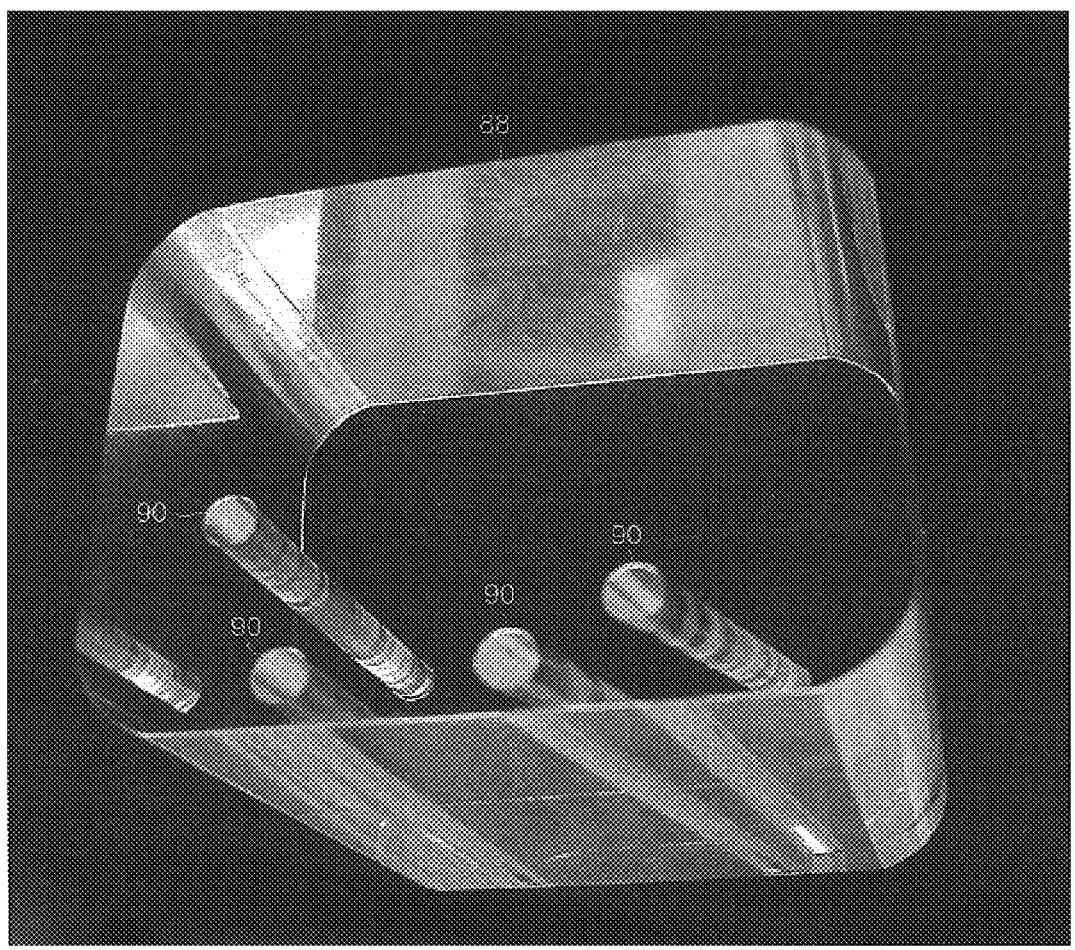
FIG. 24 is a wrist phantom for use in collecting sample data in the setup shown in FIG. 23.

In order to determine the effect of attenuation on the sensitivity of the detector array 22, a Lucite® block 88, as shown in FIG. 24, is preferably used to simulate a human wrist. The block 26 preferably includes one or more holes in the center large enough to accommodate Tygon® tubing to simulate arteries. The block 88 is preferably about 4.5 cm in thickness, which is consistent with the average thickness of the human wrist. The tubing 90 preferably runs through the block 88, which is placed between the detector arrays 12, as shown in FIG. 23.

Figure 24A:
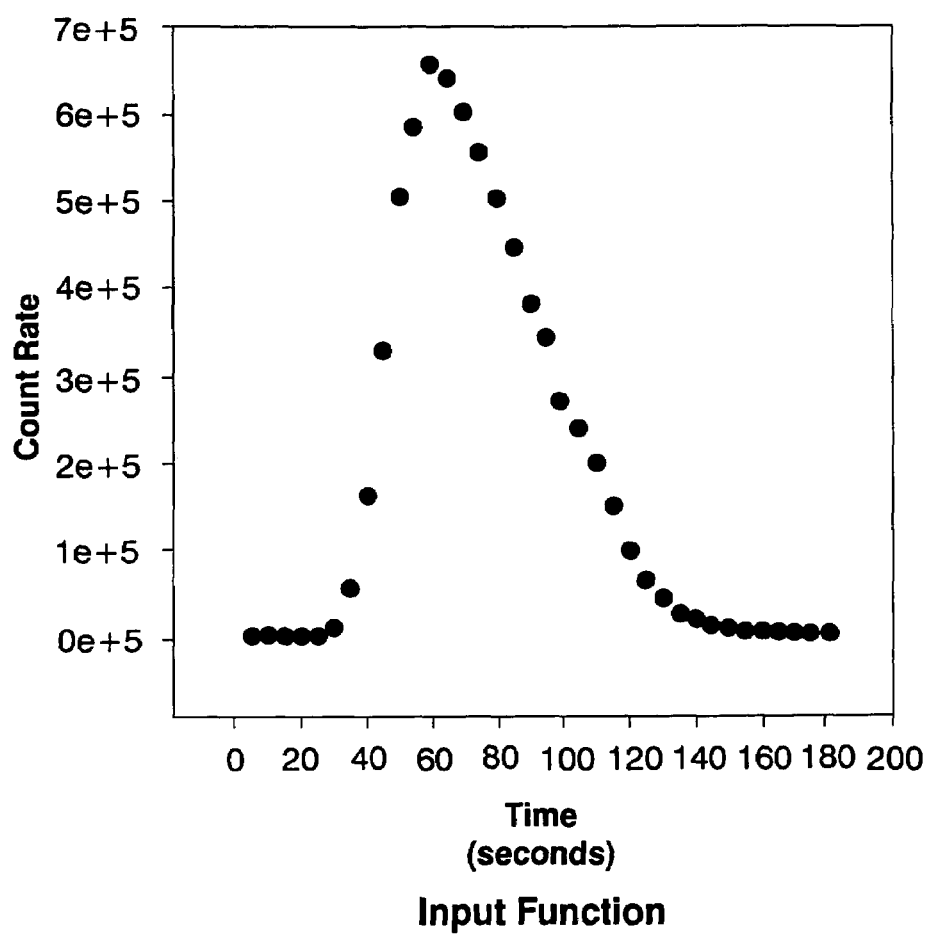
FIG. 24a is a graph of an input function obtained by the wrist detector formed in accordance with the present invention.

A series of simulated input functions is preferably acquired. An example of an input function is shown in the graph of FIG. 24a. The block 88 is then removed and similar data is preferably reacquired. Experimental results show that the only difference between the two configurations was the block 88 and attenuation effects from the block 88 produced a 27% reduction in the sensitivity of the measurements.

The wrist phantom block 88 is preferably fitted with tubing 90 chosen to closely parallel the diameter of both arteries. A solution of F-18 fluoride is preferably pumped through the tubing 90 while data is acquired using the system described above. Using this phantom, a sensitivity of about 0.04 cps/nCi/cc was obtained.

Simulations are preferably performed using estimates of the noise established from typical count rates associated with the dynamic phantom experiments described above. The purpose of these simulations was to determine the magnitude of the error introduced by using data with a similar uncertainty to that which would be expected from a single pair of crystal arrays used in the wrist detector formed in accordance with the present invention.

Figure 25:
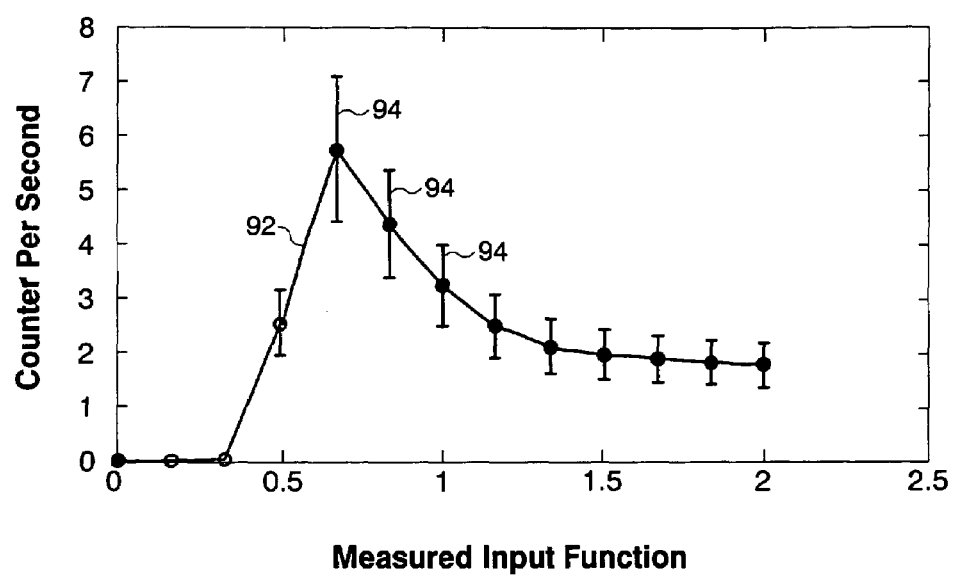
FIG. 25 is an arterial blood curve obtained using an automatic blood-sampling device.

In these experiments, an actual arterial blood curve, which was obtained using an automatic blood-sampling device and shown as a solid line 92 in FIG. 25, was used to calculate global glucose metabolic values using the Sokoloff model. Noise based on the expected uncertainties determined in the experimental measurement of the count rates is then preferably added to the blood curve using a random noise generator, which is represented as error bars 94 in FIG. 25. The simulated blood curves are preferably used to calculate metabolic values in the presence of noise introduced by the wrist detector.

Ten input function curves were generated based on the expected signal to noise ratio for the wrist detector. The values obtained for whole brain metabolism using these data showed about a 3% uncertainty in the glucose metabolic rate. This fits well within the 8% uncertainty typical of clinical PET studies. The error bars 94 may be reduced by a factor of two by increasing the detectors by a factor of four.

Figure 26:
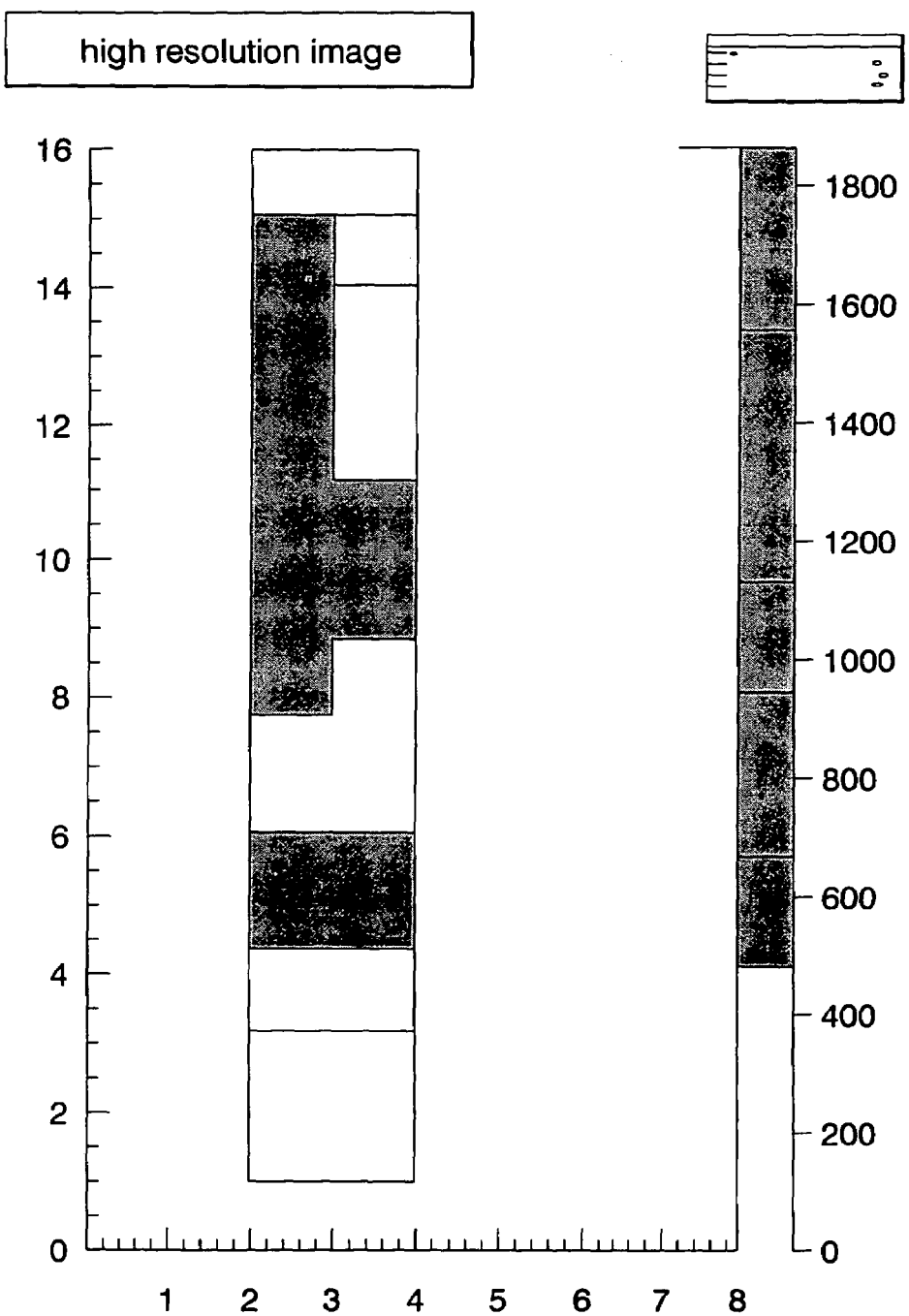
FIG. 26 is a rectilinear image of the wrist phantom shown in FIG. 24.

A planar image of the line source is preferably used to estimate the spatial resolution of the block detector system. A rectilinear image of the wrist phantom is shown in FIG. 26. Radioactivity is preferably decayed in the tubing to simulate a long acquisition image. The image is preferably used to identify regions of interest in the wrist that can then be used to generate the input function.

Figure 26A:
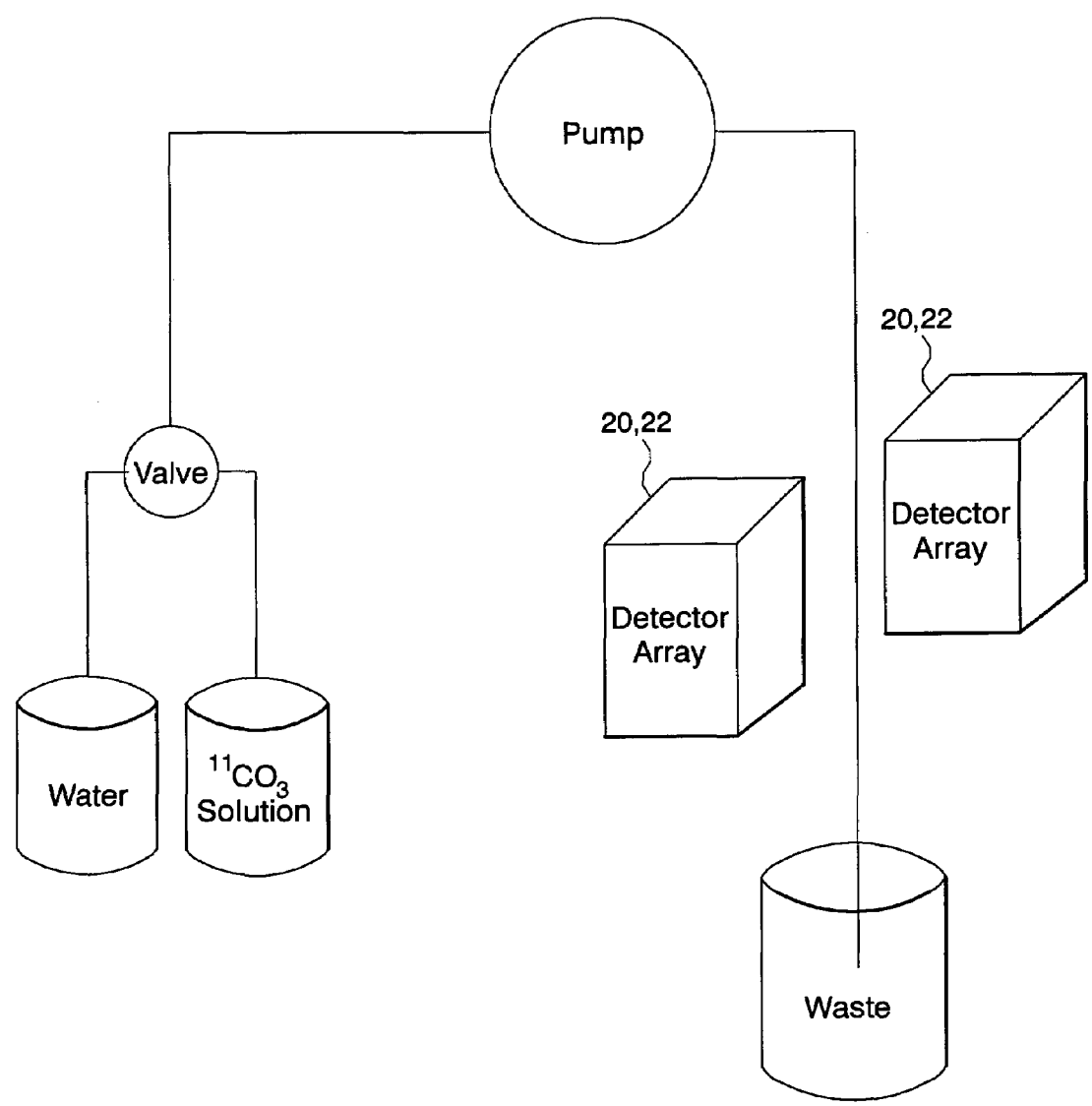
FIG. 26a is a block diagram of a test setup used to measure radioisotope activity between two detector blocks.

One of the most difficult problems in measuring arterial radioactivity is its separation from venous circulation. A typical adult radial artery is about 2 to 3 mm in diameter. The 2 mm resolution of the directly coupled detectors is preferably used to separate an arterial signal from a venous signal. The range within which the artery is distinguishable from the vein is preferably defined using the wrist phantom. Such an experiment is preferably performed by pumping water containing a positron emitting radionuclide, such as fluorine-18 or carbon-11, through silicone tubing that has been placed in the channels of the wrist phantom, as shown in FIG. 26a. The radioactivity is then preferably diluted in a reservoir and returned through channels representing the veins. In this way, the arteries may be distinguished from the veins.

In a clinical setting, detector acquisition generally begins with radiotracer injection. As the radioactivity moves through the arteries in the wrist, a region of interest is preferably defined using a two-dimensional image obtained from the arteries alone. Once this image has been obtained, the pixels corresponding to the image are preferably included in the signal for the arterial input function. The experiments involving the wrist phantom provide information concerning the spatial resolution required to obtain data exclusively from the artery while minimizing interference from the vein. It is also anticipated that the venous signal may be subtracted from the mixed signal, thereby improving the accuracy of the arterial input function.

Several approaches may be used to maximize the detected signal. The first is to determine the count rate from the wrist phantom using radioactivity levels in the tubing that are similar to levels of radioactivity present during a typical PET scan. The wrist phantom is preferably used to measure count rate and determine the optimum geometry that can be used to maximize signal-to-noise ratio. This yields an optimal position of the detectors so that the signal from the artery is high while the signal from the vein is low. The optimal position of the two detectors is preferably determined for both the radial and ulnar arteries.

In an alternative embodiment, the wrist phantom preferably includes one pair of detectors on the ulnar artery and an additional pair of detectors on the radial artery. Yet another pair of detectors running along the length of both the radial and the ulnar arteries may also be used. This provides a sum of four detector pairs, each of which preferably counts in coincidence. The arterial input function is then preferably determined using the sum of the artery signal from the radial artery and the ulner artery. This approach maximizes the signal while preserving resolution to separate the arterial signal from the venous signal.

Provided the geometry can be fixed and the attenuation generated by the wrist can be determined, quantitative information necessary to obtain a useful input function is preferably available directly from the detector. The arterial input function may alternatively be normalized to venous samples obtained at a time when arterial and venous blood are in equilibrium with respect to radioactivity concentrations.

Noise in the electronics and readout system of the wrist detector represents a major limitation to timing resolution. Therefore, the Application Specific Integrated Circuit (ASIC) shown in FIGS. 2a, 2b, 4, and 13–22 is preferably substituted for discrete devices in the wrist detector. The ASIC preferably uses 0.18 µm Complementary Metal Oxide Semiconductor (CMOS) technology, as described in P. van Zant, *Microchip Fabrication*, $3^{rd}$ Edition, pp. 99–118 (1997), which is incorporated herein by reference, and is about 1.5×4.2 mm$^2$.

Substitution of the ASIC significantly improves timing resolution. Current experimental data indicate a resolution of about 5 nanoseconds FWHM for the detector without the ASIC. FIG. 27 is a graph representing the timing resolution or Root Mean Square (RMS) zero crossing jitter from the wrist detector with the ASIC formed in accordance with the present invention.

As indicated in FIG. 27, for about 1000–2000 photoelectrons produced with a gain of 50 in the APD detector array and a peaking time of about 70 nanoseconds, the timing resolution is about 1 nanosecond. Therefore, with a coincidence timing resolution of 1 to 2 nanoseconds, much of the interference generated from random noise during acquisition of the input function can be eliminated.

The light output of the detector array is preferably measured by coupling each array to the APD detector array. A $^{22}$Na source is preferably positioned in front of the detector array and an energy pulse height spectrum is recorded for each channel. The peak position is then preferably measured, gain-corrected, and averaged for each LSO crystal array. The unbonded reflector shows a higher light output than a bonded array having the same length and manufacturer.

A reflective mask is preferably positioned on the end of the crystal array that is in contact with the APD. The light output of the detector is increased by allowing light only through an aperture that exactly matches the sensitive area of the APD detector array. A mask cut from reflective coating (available from 3M Corporation, St. Paul, Minn. 55144) is preferably used to enhance light gain in the crystal arrays, which improves both energy and timing resolution.

As shown in FIG. 10, the ASIC preferably includes access to analog signals, which are preferably brought off the chip and used externally to measure energy. As shown in FIGS. 10 and 11, the preferred embodiment of the wrist detector includes a zero crossing discriminator (ZCD) or constant fraction discriminator (CFD) per channel and the data is transferred over a serial link from the ASIC on the wrist detector to a TDC near the patient. The TDC preferably adds an absolute time stamp and sends the time-of-occurrence, channel address, and block address information to a remote coincidence processor 12, as shown in FIG. 1. A Versa Module Europa (VME) bus system is preferably used to increase the data transfer capability from the detectors to the remote coincidence processor 12. The VME bus preferably includes a TTL-based backplane which, although the system is asynchronous, sets the data transfer speed to about 20 Mbytes per second.

A single incident gamma ray that causes signals in more than one readout channel may generate cross talk between crystals. Cross talk may reduce spatial energy, and time resolution, both of which are critical. Cross talk is typically caused by Compton scattering from one crystal to another or the escape of photoelectrons from the primary crystal following absorption. In addition, for practical reasons, optical isolation of the scintillation photons within a single crystal is never perfect. Each of these effects may increase as crystal size is reduced.

The degree of cross talk has particularly important implications in the design of front-end electronics. If all of the gamma-ray signal is contained within one crystal, there is theoretically no need for energy digitization since an energy window is enforced via simple discriminator thresholds for each crystal.

Figure 28:
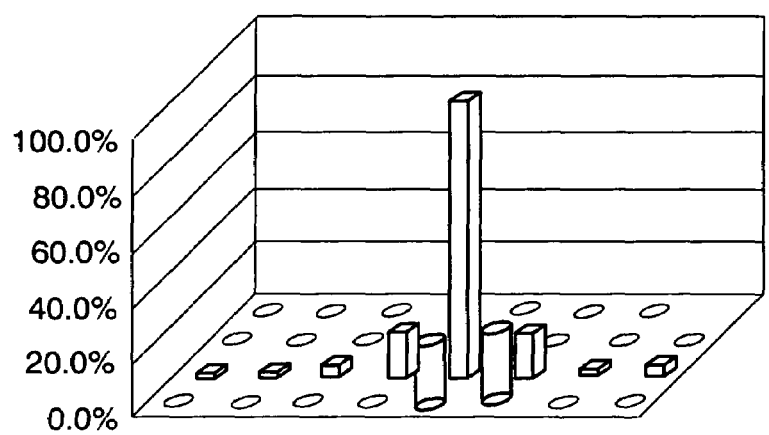
FIG. 28 is a distribution of cross-talk signals for a selected crystal in a scintillation array.

One method that is preferably used to overcome cross talk is to sum the energy in the nearest neighbor crystals to recover the complete energy deposited by the photon. This method requires analog information to be collected concerning each detector. Simulations have been performed in accordance with this technique and the results are shown in FIG. 28, which depicts the distribution of cross-talk signals for a selected crystal. A quantitative measurement of cross talk is the increase in signal produced by the inclusion of adjacent crystals.

It is to be noted that there is less cross-talk between crystals separated by a continuous reflector sheet (along the long axis) than between crystals separated by narrow, cut reflector strips (along the short axis). There is about a 25% increase in coincidence sensitivity when using the combined signals, which is preferably achieved by adding the analog pulse height information to the readout chip. Improvements in the placement of reflective sheets also decrease the amount of cross talk.

Concerning detector sensitivity, simulations performed using the expected signal-to-noise ratio generated from a single set of crystals provides about a 3% average error in the glucose metabolic rate. Increased sensitivity and reduced uncertainty are preferably achieved by using additional and/or deeper crystals.

Concerning background radioactivity from the nearby body and surrounding wrist tissue, specifically designed shielding combined with the high resolution of the wrist detector formed in accordance with the present invention selectively reduces or compensate for this interference. In addition, fast coincidence timing resolution minimizes these background effects.

Concerning interference from venous blood, which is in close anatomic proximity to the arteries from which the input function is obtained, the high resolution of the detectors combined with simultaneous measurement of venous radioactivity and subtraction of this parameter from the arterial signal enhance the ability to accurately measure the arterial input function.

Thus, the method and apparatus formed in accordance with the present invention may be used to non-invasively, selectively, and accurately measure arterial radioactivity curves for PET radiotracers with low-power requirements and low noise. The method and apparatus is able to generate an arterial input function that greatly reduces biohazards associated with blood withdrawal, as well as discomfort associated with arterial cannulation, which is useful in quantitative PET tracer studies in clinical research and diagnosis. The method and apparatus also maximize detector efficiency and spatial resolution by separating arterial information from venous and surrounding tissue information.

Although illustrative embodiments of the present invention have been described herein with reference to the accompanying drawing, it is to be understood that the invention is not limited to those precise embodiments, and that various other changes and modifications may be effected therein by one skilled in the art without departing from the scope or spirit of the invention.

The invention claimed is:

1. A method of serially transferring annihilation information in a compact positron emission tomography (PET) scanner used to obtain an input function from at least a portion of a human body, comprising the steps of:
inputting a first time pulse on a first channel, the first channel being one of a plurality of channels, the first time pulse comprising a position representing a time-of-occurrence of a first annihilation event;
generating a first time signal, the first time signal representing a time-of-occurrence of the first time pulse, the first time pulse being asynchronous to a clock signal;
generating a first address signal, the first address signal comprising a first address, the first address representing the first channel, the first address signal being synchronous to the clock signal;
generating a first channel signal, the first channel signal comprising the first time signal and the first address signal; and
outputting the first channel signal serially.

2. A method of transferring annihilation information in a compact positron emission tomography (PET) scanner used to obtain an input function from at least a portion of a human body, as defined by claim 1, further comprising the steps of:
inputting a second time pulse on a second channel, the second channel being one of the plurality of channels, the second time pulse comprising a position representing a time-of-occurrence of a second annihilation event;
generating a second time signal, the second time signal representing a time-of-occurrence of the second time pulse, the second time pulse being asynchronous to the clock signal;
generating a second address signal, the second address signal comprising a second address, the second address representing the second channel, the second address signal being synchronous to the clock signal;
generating a second channel signal, the second channel signal comprising the second time signal and the second address signal;
generating a composite signal, the composite signal comprising the first channel signal and the second channel signal; and
outputting the composite signal serially.

3. A method of transferring annihilation information in a compact positron emission tomography (PET) scanner used to obtain an input function from at least a portion of a human body, as defined by claim 1, further comprising the step of adapting the method for use in obtaining the input function from at least one of a human wrist, head, neck, arm, and leg.

4. A method of transferring annihilation information in a compact positron emission tomography (PET) scanner used to obtain an input function from at least a portion of a human body, as defined by claim 1, further comprising the steps of:
inputting first energy information on the first channel, the first energy information representing an energy content of the first annihilation event;
generating a first energy signal, the first energy signal comprising a first energy pulse, the first energy pulse comprising a position representing the first energy information, the first energy pulse being asynchronous to the clock signal; and
incorporating the first energy signal in the first channel signal.

5. A method of transferring annihilation information in a compact positron emission tomography (PET) scanner used to obtain an input function from at least a portion of a human body, as defined by claim 2, further comprising the steps of:
inputting second energy information on the second channel, the second energy information representing an energy content of the second annihilation event;
generating a second energy signal, the second energy signal comprising a second energy pulse, the second energy pulse comprising a position representing the second energy information, the second energy pulse being asynchronous to the clock signal; and
incorporating the second energy signal in the second channel signal.

6. A method of transferring annihilation information in a compact positron emission tomography (PET) scanner used to obtain an input function from at least a portion of a human body, as defined by claim 1, further comprising the step of incorporating a synchronous delay between the first time signal and the first address signal.

7. A method for serially transferring annihilation information in a compact positron emission tomography (PET) scanner used to obtain an input function from at least a portion of a human body, as defined by claim 1, wherein the first channel signal comprises a first packet, the first packet comprising information representing the first time signal and the first address signal, the method further comprising the step of determining a duration of the packet $T_{packet}$ in accordance with the following equation:

$$T_{packet} = (\log_2(N)+2) * T_{clock} \quad (1),$$

N representing the number of channels, $T_{clock}$ representing a period of the clock signal.

8. A method of transferring annihilation information in a compact positron emission tomography (PET) scanner used to obtain an input function from at least a portion of a human body, as defined by claim 1, wherein the first channel signal comprises a first packet, the first packet comprising information representing the first time signal and the first address signal, the method further comprising the step of determining a duration of the packet $T_{packet}$ in accordance with the following equation:

$$T_{packet} << 1/(N*\text{rate}) \quad (2),$$

N representing the number of channels, rate representing an average rate of annihilation events per channel.

9. A method of serially transferring annihilation information in a compact positron emission tomography (PET)

scanner used to obtain an input function from at least a portion of a human body, as defined by claim 1, further comprising the steps of:

inputting a second time pulse on a second channel, the second channel being one of the plurality of channels, the second time pulse comprising a position representing a time-of-occurrence of a second annihilation event, the time-of-occurrence of the first annihilation event being substantially the same as the time-of-occurrence of the second annihilation event; and disregarding one of the first annihilation event and the second annihilation event in accordance with a priority scheme.

10. A method of serially transferring annihilation information in a compact positron emission tomography (PET) scanner used to obtain an input function from at least a portion of a human body, as defined by claim 1, further comprising the steps of:

inputting a second time pulse on a second channel, the second channel being one of the plurality of channels, the second time pulse comprising a position representing a time-of-occurrence of a second annihilation event, the time-of-occurrence of the first annihilation event being substantially the same as the time-of-occurrence of the second annihilation event; and disregarding one of the first annihilation event and the second annihilation event associated with a lower channel address.

11. An apparatus to serially transfer annihilation information in a compact positron emission tomography (PET) scanner used to obtain an input function from at least a portion of a human body, the apparatus comprising:

a first time signal generator, the first time signal generator inputting a first time pulse on a first channel, the first channel being one of a plurality of channels, the first time pulse comprising a position representing a time-of-occurrence of a first annihilation event, the first time signal generator generating a first time signal, the first time signal representing a time-of-occurrence of the first time pulse, the first time pulse being asynchronous to a clock signal;

a first address signal generator, the first address signal generator generating a first address, the first address representing the first channel, the first address signal generator generating a first address signal, the first address signal comprising the first address, the first address signal being synchronous to the clock signal; and a first channel signal generator, the first channel signal generator generating a first channel signal, the first channel signal comprising the first time signal and the first address signal, the first channel signal generator outputting the first channel signal serially.

12. An apparatus to serially transfer annihilation information in a compact positron emission tomography (PET) scanner used to obtain an input function from at least a portion of a human body as defined by claim 11, further comprising:

a second time signal generator, the second time signal generator inputting a second time pulse on a second channel, the second channel being one of the plurality of channels, the second time pulse comprising a position representing a time-of-occurrence of a second annihilation event, the second time signal generator generating a second time signal, the second time signal representing a time-of-occurrence of the second time pulse, the second time pulse being asynchronous to the clock signal;

a second address signal generator, the second address signal generator generating a second address, the second address representing the second channel, the second address signal generator generating a second address signal, the second address signal comprising the second address, the second address signal being synchronous to the clock signal; and a second channel signal generator, the second channel signal generator generating a second channel signal, the second channel signal comprising the second time signal and the second address signal, the second channel signal generator generating a composite signal, the composite signal comprising the first channel signal and the second channel signal, the second channel signal generator outputting the composite signal serially.

13. An apparatus to serially transfer annihilation information in a compact positron emission tomography (PET) scanner used to obtain an input function from at least a portion of a human body as defined by claim 11, wherein the first time signal generator inputs a second time pulse on a second channel, the second channel being one of the plurality of channels, the second time pulse comprising a position representing a time-of-occurrence of a second annihilation event, the first time signal generator generating a second time signal, the second time signal representing a time-of-occurrence of the second time pulse, the second time pulse being asynchronous to the clock signal, the first address signal generator generating a second address, the second address representing the second channel, the first address signal generator generating a second address signal, the second address signal comprising the second address, the second address signal being synchronous to the clock signal, the first channel signal generator generating a second channel signal, the second channel signal comprising the second time signal and the second address signal, the first channel signal generator generating a composite signal, the composite signal comprising the first channel signal and the second channel signal, the first channel signal generator outputting the composite signal serially.

14. An apparatus to serially transfer annihilation information in a compact positron emission tomography (PET) scanner used to obtain an input function from at least a portion of a human body as defined by claim 11, wherein the apparatus is adapted for use in obtaining the input function from least one of a human wrist, head, neck, arm, and leg.

15. An apparatus to serially transfer annihilation information in a compact positron emission tomography (PET) scanner used to obtain an input function from at least a portion of a human body as defined by claim 11, further comprising a first energy signal generator, the first energy signal generator inputting first energy information on the first channel, the first energy information comprising an energy content of the first annihilation event, the first energy signal generator generating a first energy signal, the first energy signal comprising a first energy pulse, the first energy pulse comprising a position representing the first energy information, the first energy pulse being asynchronous to the clock signal, the first channel signal generator incorporating the first energy signal in the first channel signal.

16. An apparatus to serially transfer annihilation information in a compact positron emission tomography (PET) scanner used to obtain an input function from at least a portion of a human body as defined by claim 12, further comprising a second energy signal generator, the second energy signal generator inputting second energy information on the second channel, the second energy information comprising an energy content of the second annihilation event, the second energy signal generator generating a second energy signal, the second energy signal comprising a second energy pulse, the second energy pulse comprising a position representing the second energy information, the second energy pulse being asynchronous to the clock signal, the second channel signal generator incorporating the second energy signal in the second channel signal.

17. An apparatus to serially transfer annihilation information in a compact positron emission tomography (PET) scanner used to obtain an input function from at least a portion of a human body as defined by claim 15, wherein the first energy signal generator inputs second energy information on the first channel, the second energy information comprising an energy content of the second annihilation event, the first energy signal generator generating a second energy signal, the second energy signal comprising a second energy pulse, the second energy pulse comprising a position representing second energy information, the second energy pulse being asynchronous to the clock signal, the first channel signal generator incorporating the second energy signal in the first channel signal.

18. An apparatus to serially transfer annihilation information in a compact positron emission tomography (PET) scanner used to obtain an input function from at least a portion of a human body as defined by claim 11, wherein the first channel signal generator incorporates a synchronous delay between the first time signal and the first address signal.

19. An apparatus to serially transfer annihilation information in a compact positron emission tomography (PET) scanner used to obtain an input function from at least a portion of a human body as defined by claim 11, wherein the first channel signal generator generates a first packet, the first packet comprising information representing the first time signal and the first address signal, the first signal generator determining a duration of the packet $T_{packet}$ in accordance with the following equation:

$$T_{packet} = (\log_2(N)+2)*T_{clock} \quad (1),$$

N representing the number of channels, $T_{clock}$ representing a period of the clock signal.

20. An apparatus to serially transfer annihilation information in a compact positron emission tomography (PET) scanner used to obtain an input function from at least a portion of a human body as defined by claim 11, wherein the first channel signal generator generates a first packet, the first packet comprising information representing the first time signal and the first address signal, the first channel signal generator determining a duration of the packet $T_{packet}$ in accordance with the following equation:

$$T_{packet} << 1/(N*\text{rate}) \quad (2),$$

N representing the number of channels, rate representing an average rate of annihilation events per channel.

21. An apparatus to serially transfer annihilation information in a compact positron emission tomography (PET) scanner used to obtain an input function from at least a portion of a human body as defined by claim 11, further comprising:
a second time signal generator, the second time signal generator inputting a second time pulse on a second channel, the second channel being one of the plurality of channels, the second time pulse comprising a position representing a time-of-occurrence of a second annihilation event, the time-of-occurrence of the first annihilation event being substantially the same as the time-of-occurrence of the second annihilation event; and
a priority encoder, the priority encoder disregarding one of the first annihilation event and the second annihilation event in accordance with a priority scheme.

22. An apparatus to serially transfer annihilation information in a compact positron emission tomography (PET) scanner used to obtain an input function from at least a portion of a human body as defined by claim 11, further comprising:
a second time signal generator, the second time signal generator inputting a second time pulse on a second channel, the second channel being one of the plurality of channels, the second time pulse comprising a position representing a time-of-occurrence of a second annihilation event, the time-of-occurrence of the first annihilation event being substantially the same as the time-of-occurrence of the second annihilation event; and
a priority encoder, the priority encoder disregarding one of the first annihilation event and the second annihilation event associated with a lower channel address.

23. An apparatus to serially transfer annihilation information in a compact positron emission tomography (PET) scanner used to obtain an input function from at least a portion of a human body as defined by claim 11, wherein the apparatus is adapted for implementation in an Application Specific Integrated Circuit (ASIC).

24. An apparatus to serially transfer annihilation information in a compact positron emission tomography (PET) scanner used to obtain an input function from at least a portion of a human body as defined by claim 11, wherein the first time signal generator comprises a flip-flop, the flip flop being clocked by the first time pulse, the flip flop outputting the first time signal.

25. An apparatus to serially transfer annihilation information in a compact positron emission tomography (PET) scanner used to obtain an input function from at least a portion of a human body as defined by claim 11, wherein the first address signal generator comprises a shift register, the shift register being loaded with the first address in response to the first time signal, the shift register being clocked by the clock signal.

26. An apparatus to serially transfer annihilation information in a compact positron emission tomography (PET) scanner used to obtain an input function from at least a portion of a human body as defined by claim 11, wherein the first channel signal generator comprises combinatorial logic, the combinatorial logic incorporating the first time signal and the first address signal in the first channel signal.

27. A compact positron emission tomography (PET) scanner used to obtain an input function from at least a portion of a human body, the scanner comprising:
a scintillation array, the scintillation array comprising a first crystal, the first crystal being one of a plurality of crystals in the scintillation array, the first crystal being associated with a first channel, the first crystal outputting at least one photon in response to receiving gamma radiation from a first annihilation event;
a detection array, the detection array comprising a first detector, the first detector being one of a plurality of detectors in the detection array, the first detector being associated with the first channel, the first detector outputting a first detection signal in response to detecting the at least one photon;

a front-end array, the front end array comprising a first front end, the first front end being one of a plurality of front ends in the front end array, the first front end being associated with the first channel, the first front end outputting a first time pulse in response to receiving the first detection signal;

a first serial encoder, the first serial encoder being associated with the first channel, the first serial encoder comprising:

a first time signal generator, the first time signal generator inputting the first time pulse on the first channel, the first channel being one of a plurality of channels, the first time pulse comprising a position representing a time-of-occurrence of a first annihilation event, the first time signal generator generating a first time signal, the first time signal representing a time-of-occurrence of the first time pulse, the first time pulse being asynchronous to a clock signal;

a first address signal generator, the first address signal generator generating a first address, the first address representing the first channel, the first address signal generator generating a first address signal, the first address signal comprising the first address, the first address signal being synchronous to the clock signal; and a first channel signal generator, the first channel signal generator generating a first channel signal, the first channel signal comprising the first time signal and the first address signal, the first channel signal generator outputting the first channel signal serially.

28. A compact positron emission tomography (PET) scanner used to obtain an input function from at least a portion of a human body as defined by claim 27, further comprising a second serial encoder, the second serial encoder being associated with a second channel, the second serial encoder comprising:

a second time signal generator, the second time signal generator inputting a second time pulse on the second channel, the second channel being one of the plurality of channels, the second time pulse comprising a position representing a time-of-occurrence of a second annihilation event, the second time signal generator generating a second time signal, the second time signal representing a time-of-occurrence of the second time pulse, the second time pulse being asynchronous to the clock signal;

a second address signal generator, the second address signal generator generating a second address, the second address representing the second channel, the second address signal generator generating a second address signal, the second address signal comprising the second address, the second address signal being synchronous to the clock signal; and a second channel signal generator, the second channel signal generator generating a second channel signal, the second channel signal comprising the second time signal and the second address signal, the second channel signal generator generating a composite signal, the composite signal comprising the first channel signal and the second channel signal, the second channel signal generator outputting the composite signal serially.

29. A compact positron emission tomography (PET) scanner used to obtain an input function from at least a portion of a human body as defined by claim 27, wherein the first time signal generator inputs a second time pulse on a second channel, the second channel being one of the plurality of channels, the second time pulse comprising a position representing a time-of-occurrence of a second annihilation event, the first time signal generator generating a second time signal, the second time signal representing a time-of-occurrence of the second time pulse, the second time pulse being asynchronous to the clock signal, the first address signal generator generating a second address, the second address representing the second channel, the first address signal generator generating a second address signal, the second address signal comprising the second address, the second address signal being synchronous to the clock signal, the first channel signal generator generating a second channel signal, the second channel signal comprising the second time signal and the second address signal, the first channel signal generator generating a composite signal, the composite signal comprising the first channel signal and the second channel signal, the first channel signal generator outputting the composite signal serially.

30. A compact positron emission tomography (PET) scanner used to obtain an input function from at least a portion of a human body as defined by claim 27, wherein the first front end further comprises at least one of a preamplifier, a shaper network, a zero-crossing detector, and a constant fraction discriminator.

31. A compact positron emission tomography (PET) scanner used to obtain an input function from at least a portion of a human body as defined by claim 27, wherein the scanner is adapted for use in obtaining the input function from at least one of a human wrist, head, neck, arm, and leg.

32. A compact positron emission tomography (PET) scanner used to obtain an input function from at least a portion of a human body as defined by claim 27, wherein the first serial encoder further comprises a first energy signal generator, the first energy signal generator inputting first energy information on the first channel, the first energy information comprising an energy content of the first annihilation event, the first energy signal generator generating a first energy signal, the first energy signal comprising a first energy pulse, the first energy pulse comprising a position representing the first energy information, the first energy pulse being asynchronous to the clock signal, the first channel signal generator incorporating the first energy signal in the first channel signal.

33. A compact positron emission tomography (PET) scanner used to obtain an input function from at least a portion of a human body as defined by claim 28, wherein the second serial encoder further comprises a second energy signal generator, the second energy signal generator inputting second energy information on the second channel, the second energy information comprising an energy content of the second annihilation event, the second energy signal generator generating a second energy signal, the second energy signal comprising a second energy pulse, the second energy pulse comprising a position representing the second energy information, the second energy pulse being asynchronous to the clock signal, the second channel signal generator incorporating the second energy signal in the second channel signal.

34. A compact positron emission tomography (PET) scanner used to obtain an input function from at least a portion of a human body as defined by claim 32, wherein the first energy signal generator inputs second energy information on a second channel, the second energy information comprising an energy content of a second annihilation event, the first energy signal generator generating a second energy signal, the second energy signal comprising a second energy pulse, the second energy pulse comprising a position representing the second energy information, the second energy pulse being asynchronous to the clock signal, the first channel signal generator incorporating the second energy signal in the first channel signal.

35. A compact positron emission tomography (PET) scanner used to obtain an input function from at least a portion of a human body as defined by claim 27, wherein the first channel signal generator generates a first packet, the first packet comprising information representing the first time signal and the first address signal, the first channel signal generator determining a duration of the packet $T_{packet}$ in accordance with the following equation:

$$T_{packet} << 1/(N*\text{rate}) \qquad (2),$$

N representing the number of channels, rate representing an average rate of annihilation events per channel.

36. A compact positron emission tomography (PET) scanner used to obtain an input function from at least a portion of a human body as defined by claim 27, further comprising:
   a second serial encoder, the second serial encoder being associated with a second channel, the second serial encoder comprising a second time signal generator, the second time signal generator inputting a second time pulse on a second channel, the second channel being one of the plurality of channels, the second time pulse comprising a position representing a time-of-occurrence of a second annihilation event, the time-of-occurrence of the first annihilation event being substantially the same as the time-of-occurrence of the second annihilation event; and
   a priority encoder, the priority encoder disregarding one of the first annihilation event and the second annihilation event in accordance with a priority scheme.

37. A compact positron emission tomography (PET) scanner used to obtain an input function from at least a portion of a human body as defined by claim 27, further comprising:
   a second serial encoder, the second serial encoder being associated with a second channel, the second serial encoder comprising a second time signal generator, the second time signal generator inputting a second time pulse on a second channel, the second channel being one of the plurality of channels, the second time pulse comprising a position representing a time-of-occurrence of a second annihilation event, the time-of-occurrence of the first annihilation event being substantially the same as the time-of-occurrence of the second annihilation event; and
   a priority encoder, the priority encoder disregarding one of the first annihilation event and the second annihilation event associated with a lower channel address.

38. A compact positron emission tomography (PET) scanner used to obtain an input function from at least a portion of a human body as defined by claim 27, wherein the front-end array and the first serial encoder are adapted for implementation in an Application Specific Integrated Circuit (ASIC).

39. A compact positron emission tomography (PET) scanner used to obtain an input function from at least a portion of a human body as defined by claim 27, wherein the scintillation array comprises at least one Lutetium Oxyorthosilicate (LSO) crystal.

40. A compact positron emission tomography (PET) scanner used to obtain an input function from at least a portion of a human body as defined by claim 27, wherein the detector array comprises at least one avalanche photodiode (APD).

* * * * *